(12) United States Patent
Manting et al.

(10) Patent No.: US 11,052,144 B2
(45) Date of Patent: Jul. 6, 2021

(54) METHODS OF TUMOR VACCINATION

(71) Applicant: DCPRIME B.V., Leiden (NL)

(72) Inventors: Erik Hans Manting, Leiden (NL);
Satwinder Kaur Singh, Leiden (NL);
Vinod Sommandas, Leiden (NL)

(73) Assignee: DCPRIME B.V., Leiden (NL)

( * ) Notice: Subject to any disclaimer, the term of this patent is extended or adjusted under 35 U.S.C. 154(b) by 0 days.

(21) Appl. No.: 16/857,851

(22) Filed: Apr. 24, 2020

(65) Prior Publication Data

US 2020/0390876 A1 Dec. 17, 2020

Related U.S. Application Data

(60) Provisional application No. 62/961,554, filed on Jan. 15, 2020.

(30) Foreign Application Priority Data

Apr. 25, 2019 (EP) ..................... 19170999
Jul. 16, 2019 (WO) ............... PCT/NL2019/050451

(51) Int. Cl.
*A61K 39/05* (2006.01)
*A61P 35/00* (2006.01)
*A61K 39/00* (2006.01)

(52) U.S. Cl.
CPC .............. *A61K 39/05* (2013.01); *A61P 35/00* (2018.01); *A61K 2039/54* (2013.01); *A61K 2039/545* (2013.01); *A61K 2039/572* (2013.01); *A61K 2039/575* (2013.01); *A61K 2039/585* (2013.01)

(58) Field of Classification Search
None
See application file for complete search history.

(56) References Cited

U.S. PATENT DOCUMENTS

| | | | |
|---|---|---|---|
| 5,876,989 A | 3/1999 | Berg et al. | |
| 6,680,301 B2 | 1/2004 | Berg et al. | |
| 7,700,546 B2 | 4/2010 | Mekada et al. | |
| 8,507,443 B2 | 8/2013 | Mekada et al. | |
| 2004/0057935 A1 | 3/2004 | Yu et al. | |
| 2013/0330399 A1 | 12/2013 | Reisfeld et al. | |

FOREIGN PATENT DOCUMENTS

| | | |
|---|---|---|
| EP | 1894575 B1 | 2/2013 |
| EP | 2931878 B1 | 11/2016 |
| WO | WO 1996/007432 A1 | 3/1996 |
| WO | WO 1996/040200 A1 | 12/1996 |
| WO | WO 2000/054802 A2 | 9/2000 |
| WO | WO 2001/049317 A2 | 7/2001 |
| WO | WO 2002/023994 A1 | 3/2002 |
| WO | WO 2002/044395 A1 | 6/2002 |
| WO | WO 2002/044396 A1 | 6/2002 |
| WO | WO 2002/080648 A2 | 10/2002 |
| WO | WO 2003/020309 A2 | 3/2003 |
| WO | WO 2009/019320 A2 | 2/2009 |
| WO | WO 2009/034172 A1 | 3/2009 |
| WO | WO 2009/127988 A1 | 10/2009 |
| WO | WO 2011/018636 A2 | 2/2011 |
| WO | WO 2012/136824 A1 | 10/2012 |
| WO | WO 2014/006058 A1 | 1/2014 |
| WO | WO 2014/138314 A1 | 9/2014 |
| WO | WO 2015/073801 A1 | 5/2015 |
| WO | WO 2018/017020 A1 | 1/2018 |
| WO | WO 2020/017962 A1 | 1/2020 |

OTHER PUBLICATIONS

Alemany, "Oncolytic Adenoviruses in Cancer Treatment", Biomedicines, 2014, 2(1): 36-49.
Alibakhshi et al., "Targeted cancer therapy through antibody fragments-decorated nanomedicines", J Control Release, 2017, 268: 323-334.
Andtbacka et al., "Talimogene Laherparepvec Improves Durable Response Rate in Patients With Advanced Melanoma", Journal of Clinical Oncology, 2015, 22(25): 2780-2788.
Anguille et al., "Dendritic cell vaccination as postremission treatment to prevent or delay relapse in acute myeloid leukemia", Blood, Oct. 2017, 130(15): 1713-1721.
Awate et al., "Mechanisms of Action of Adjuvants" Frontiers in Immunology, 2013, 4(114): 1-10.
Bell et al., "Crystal structure of nucleotide-free diphtheria toxin", Biochemistry, 1997, 36(3): 481-488.
Bender et al., "Inactivated influenza virus, when presented on dendritic cells, elicits human CD8* cytolytic T cell responses", J. Exp. Med, 1995, 182: 1663-1671.
Bennett et al., "Help for cytotoxic-T-cell responses is mediated by CD40 signaling", Nature, 1998, 393: 478-480.
Bergmann et al., "An endogenously synthesized decamer peptide efficiently primes cytotoxic T cells specific for the HIV-1 envelope glycoprotein", Eur J Immunol., 1993, 23(11): 2777-2781.
Bommareddy et al., "Integrating oncolytic viruses in combination cancer immunotherapy", Nature Reviews Immunology, 2018, 18: 498-513.
Buzzi et al., "Cancer immunity after treatment of Ehrlich tumor with diphtheria toxin", Cancer Res., Dec. 1974, 34(12): 3481-3486.
Buzzi et al., "CRM197: Effects of intravenous administration to advanced cancer patients", Cancer Res., Apr. 2004, 64(7 Supplement): 878.
Buzzi et al., "Diphtheria toxin in cancer therapy", The Lancet, 1974, 1(7858): 628-629.
Buzzi, "Diphtheria toxin treatment of human advanced cancer", Cancer Res., 1982, 42(5): 2054-2058.

(Continued)

*Primary Examiner* — Padmavathi Baskar
(74) *Attorney, Agent, or Firm* — Lathrop Gpm LLP; James H. Velema; Judith L. Stone-Hulslander

(57) ABSTRACT

A method for treating a tumor or generating an immune response against a tumor in a subject in need including a vaccination step comprising administration of a first composition, and a tumor-marking step comprising administration of a second composition, is provided. The first and second composition each comprises an antigenic polypeptide (e.g., a non-tumor antigen) or a nucleic acid encoding an antigenic polypeptide. Also provided are antigenic polypeptides and compositions for use in methods described herein.

20 Claims, 10 Drawing Sheets

Specification includes a Sequence Listing.

(56) References Cited

OTHER PUBLICATIONS

Buzzi, et al., "CRM197 (nontoxic diphtheria toxin): effects on advanced cancer patients", Cancer Immunol. Immunother., 2004, 53: 1041-1048 (2004).
Buzzi, et al., "CRM197 and cancer: Effects of intratumoral administration", Therapy, Sep. 2004, 1(1): 61-66.
Buzzi, et al., "CRM197; Effects of intravenous administration to advanced cancer patients", American Association for Cancer Research, 2004, 64(7), Supplement.
Cheever et al, "The prioritization of cancer antigens: a national cancer institute pilot project for the acceleration of translational research", Clin Cancer Res., 2009, 15(17): 5323-5337.
Cripe et al., "Phase 1 Study of Intratumoral Pexa-Vec (JX-594), an Oncolytic and Immunotherapeutic Vaccinia Virus, in Pediatric Cancer Patients", Molecular Therapy, 2015, 23(3): 602-608.
Davis et al., "Basic Methods in Molecular Biology," 1986.
Fiorentini, et al., "Clinical experience of treatment of metastatic melanoma and solid tumours adopting a derivative of diphtheria toxin: cross-reacting material 197", In Vivo, 2013, 27(2): 197-202.
Frietze et al., "Engineering virus-like particles as vaccine platforms", Curr Opin Virol., 2016, 18: 44-49.
Geha et al., "The genetic basis of immunoglobulin-class switching", N Engl J Med., 1994, 330(14): 1008-1009.
Graham et al., "A new technique for the assay of infectivity of human adenovirus 5 DNA", Virology, 1973, 52(2): 456-467.
Grossardt et al., "Granulocyte-macrophage colony-stimulating factor-armed oncolytic measles virus is an effective therapeutic cancer vaccine", Human Gene Therapy, 2013, 24: 644-654.
Haddad, "Genetically Engineered Vaccinia Viruses as Agents for Cancer Treatment, Imaging, and Transgene Delivery", Frontiers in Immunology, 2017, 7: 96.
He et al., "CCL3 and CCL20-recruited dendritic cells modified by melanoma antigen gene-1 induce anti-tumor immunity against gastric cancer ex vivo and in vivo", Journal of Experimental & Clinical Cancer Research, 2010, 29: 37.
Hirooka et al., "Comprehensive immunotherapy combined with intratumoral injection of zoledronate-pulsed dendritic cells, intravenous adoptive activated T lymphocyte and gemcitabine in unresectable locally advanced pancreatic carcinoma: a phase I/II trial", Oncotarget, 2018, 9(2): 2838-2847.
Howells et al., "Oncolytic Viruses—Interaction of Virus and Tumor Cells in the Battle to Eliminate Cancer", Front Oncol., 2017, 7: 195.
Hutzler et al., "Antigen-specific oncolytic MV-based tumor vaccines through presentation of selected tumor-associated antigens on infected cells or virus-like particles", Scientific Reports, 2017, 7: 16892.
International Search Report and Written Opinion for PCT International Application No. PCT/IB2020/053898, dated Jul. 2, 2020, 17 pages.
Jurincic-Winkler et al., "Antibody response to keyhole limpet hemocyanin (KLH) treatment in patients with superficial bladder carcinoma", Anticancer Res., 1996,16(4A): 2105-2110.
Kalinski et al., "Consensual immunity: success-driven development of T-helper-1 and T-helper-2 responses", Nature Reviews, Immunology, 2005, 5: 251-260.
Koup et al., "Vaccine design for CD8 T lymphocyte responses", Cold Spring Harb Perspect Med., 2011, 1(1): a007252.
Kudo-Saito, et al., "Intratumoral vaccination and diversified subcutaneous/intratumoral vaccination with recombinant poxviruses encoding a tumor antigen and multiple costimulatory molecules", Clin Cancer Res., 2004, 10(3): 1090-1099.
Lal et al., "Recombinant viruses with other anti-cancer therapeutics: a step towards advancement of oncolytic virotherapy", Cancer Gene Ther., 2018, 25: 216-226.
Laurell et al., "Intratumorally injected pro-inflammatory allogeneic dendritic cells as immune enhancers: a first-in-human study in unfavourable risk patients with metastatic renal cell carcinoma", Journal for Immunotherapy of Cancer, 2017, 5:52.

Lawler et al., "Oncolytic Viruses in Cancer Treatment: A Review", JAMA Oncol. Review, 2017, 3(6): 841-849.
Lundstrom, "Viral Vectors in Gene Therapy", Diseases, 2018, 6(2): 42.
Malito et al., "Structural basis for lack of toxicity of the diphtheria toxin mutant CRM197", Proc Natl Acad Sci U S A, 2012, 109(14): 5229-5234.
Marelli et al., "Oncolytic Viral Therapy and the Immune System: A Double-Edged Sword Against Cancer", Frontiers in Immunology, 2018, 9: 866.
Mishra et al., "Structural and immunological characterization of E. coli derived recombinant $CRM_{197}$ protein used as carrier in conjugate vaccines", Bioscience reports, 2018, 38(5): BSR20180238.
Miyamoto et al., "Heparin-binding epidermal growth factor-like growth factor as a novel targeting molecule for cancer therapy", Cancer Sci, 2006, 97(5): 341-347.
Miyamoto, et al., "New approach to cancer therapy: heparin binding-epidermal growth factor-like growth factor as a novel targeting molecule", Anticancer Res., 2007, 27(6A): 3713-3721.
Mohan et al., "Applications of chemokines as adjuvants for vaccine immunotherapy", Immunobiology, 2018, 223(6-7): 477-485.
Moya et al., "Inhibition of coated pit formation in Hep2 cells blocks the cytotoxicity of diphtheria toxin but not that of ricin toxin", J Cell Biol., 1985, 101(2): 548-559.
Nam, et al., "Anti-tumor Effect of Intravenous Administration of CRM197 for Triple-negative Breast Cancer Therapy", Anticancer Res., 2016, 36(7): 3651-3657.
Nguyen-Hoai et al., "CCL21 (SLC) improves tumor protection by a DNA vaccine in a Her2/neu mouse tumor model", Cancer Gene Therapy, 2012, 19: 69-76.
Olusanya et al., "Liposomal Drug Delivery Systems and Anticancer Drugs", Molecules, 2018, 23(4): 907.
Pashine et al., "Targeting the innate immune response with improved vaccine adjuvants", Nature Medicine Supplement, 2005, 11(4): S63-S68.
Saxena et al., "Re-emergence of Dendritic Cell Vaccines for Cancer Treatment", Trends in Cancer, 2018, 4:2: 119-137.
Stickings, et al., "Transcutaneous immunization with cross-reacting material CRM(197) of diphtheria toxin boosts functional antibody levels in mice primed parenterally with adsorbed diphtheria toxoid vaccine", Infect Immun., 2008, 76(4): 1766-1773.
Suhrbier, "Multi-epitope DNA vaccines", Immunol Cell Biol., 1997, 75(4): 402-408.
Tacken et al., "Effective induction of naive and recall T-cell responses by targeting antigen to human dendritic cells via a humanized anti-DC-SIGN antibody", Blood, 2005, 106(4): 1278-1285.
Temizoz et al., "Vaccine adjuvants as potential cancer immunotherapeutics", Int Immunol., 2016, 28(7): 329-338.
Triozzi et al., "Intratumoral injection of dendritic cells derived in vitro in patients with metastatic cancer", Cancer, 2000, 89(12): 2646-2654.
Twumasi-Boateng et al., "Oncolytic viruses as engineering platforms for combination immunotherapy", Nature Reviews Cancer, 2018, 18(7): 419-432.
Uchida et al., "Mutation in the structural gene for diphtheria toxin carried by temperate phage", Nat New Biol., 1971, 233(35): 8-11.
Ud Din et al., "Effective use of nanocarriers as drug delivery systems for the treatment of selected tumors", Int J Nanomedicine, 2017, 12: 7291-7309.
Van Nuffel et al., "Loading of dendritic cells for immunotherapy", ISBT Science Series, 2013, 8: 161-164.
Van Tendeloo et al., "Induction of complete and molecular remissions in acute myeloid leukemia by Wilms' tumor 1 antigen-targeted dendritic cell vaccination", PNAS, 2010, 107(31): 13824-13829.
Vigneron et al, "Database of T cell-defined human tumor antigens: the 2013 update", Cancer Immunity, 2013, 13: 15.
Wallgren et al., "Direct Allorecognition Promotes Activation of Bystander Dendritic Cells and Licenses Them for Th1 Priming: A Functional Link Between Direct and Indirect Allosensitization", Scandinavian Journal of Immunology, 2005, 62: 234-242.
International Search Report and Written Opinion for PCT International Application No. PCT/NL2019/050451, dated Oct. 4, 2019, 13 pages.

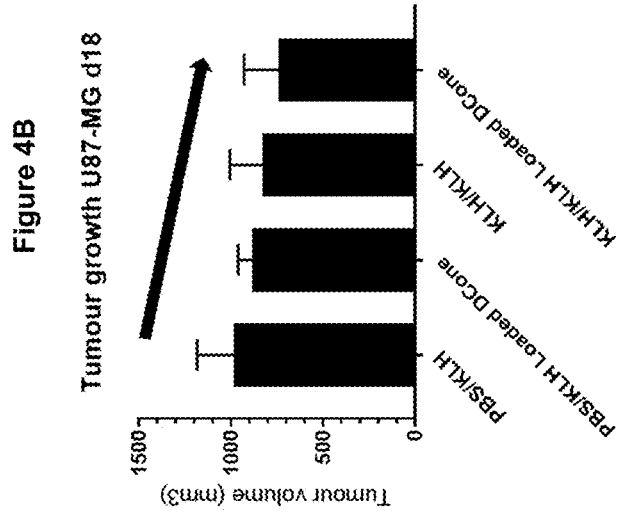
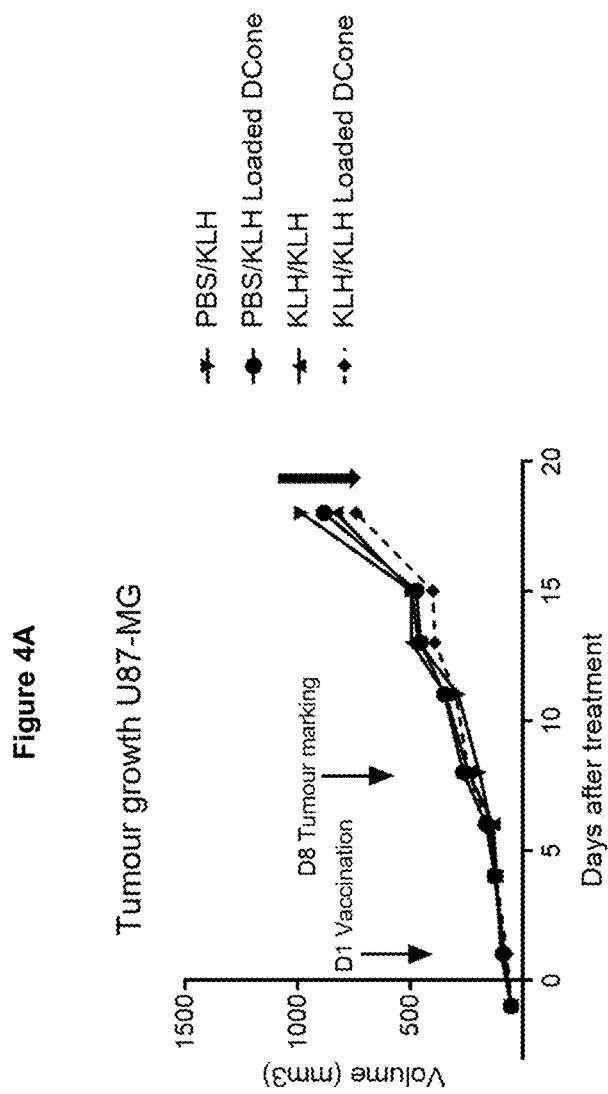
Figure 4B
Figure 4A

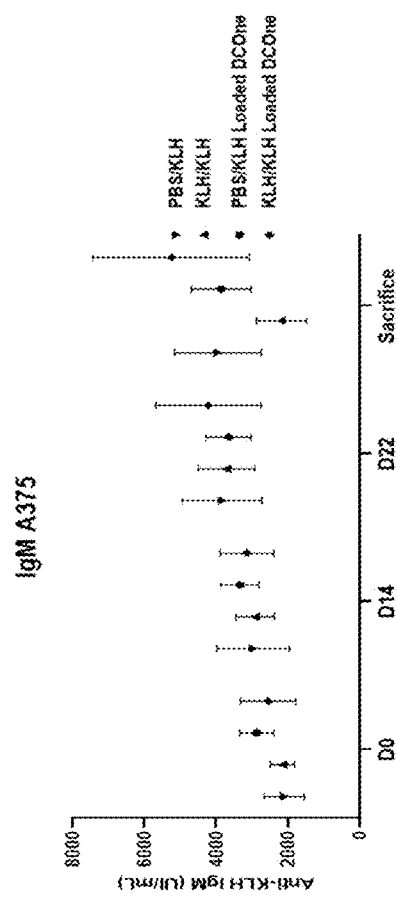
Figure 6A
Figure 6B
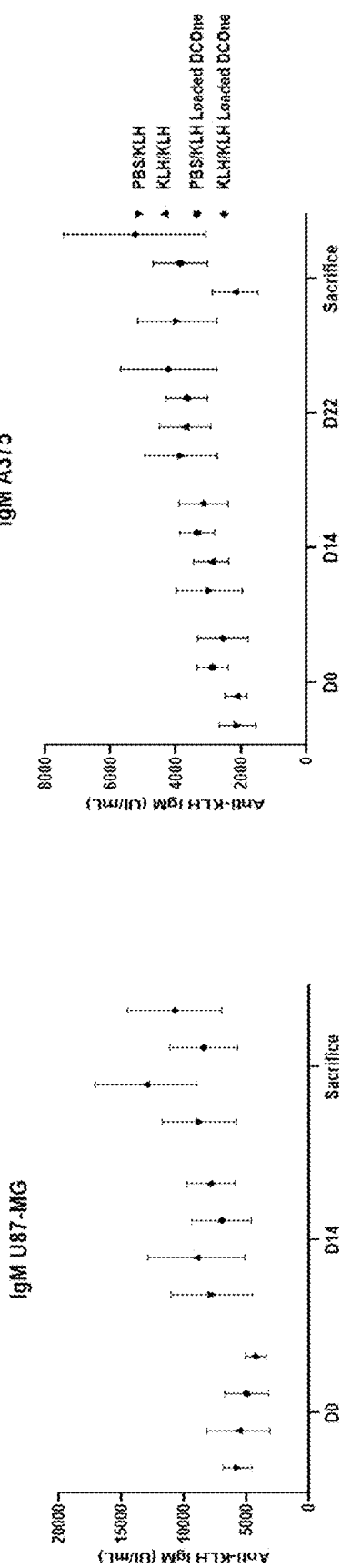
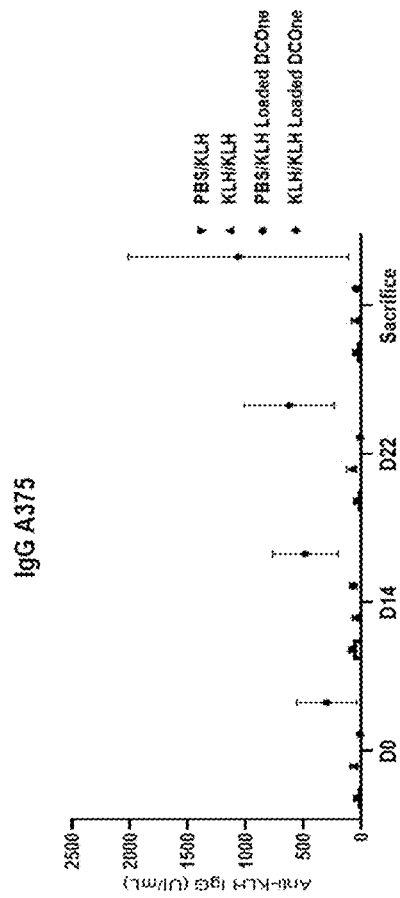
Figure 6C
Figure 6D
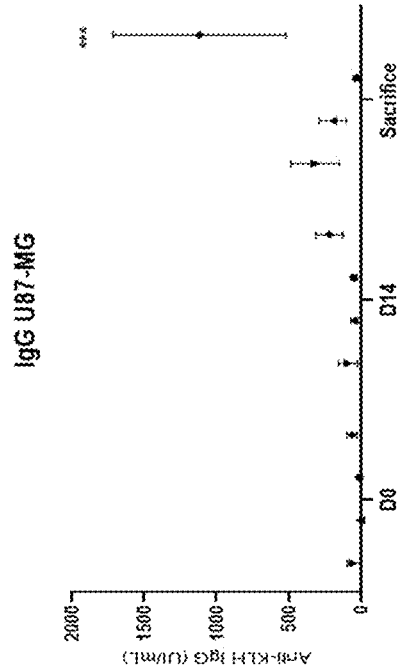

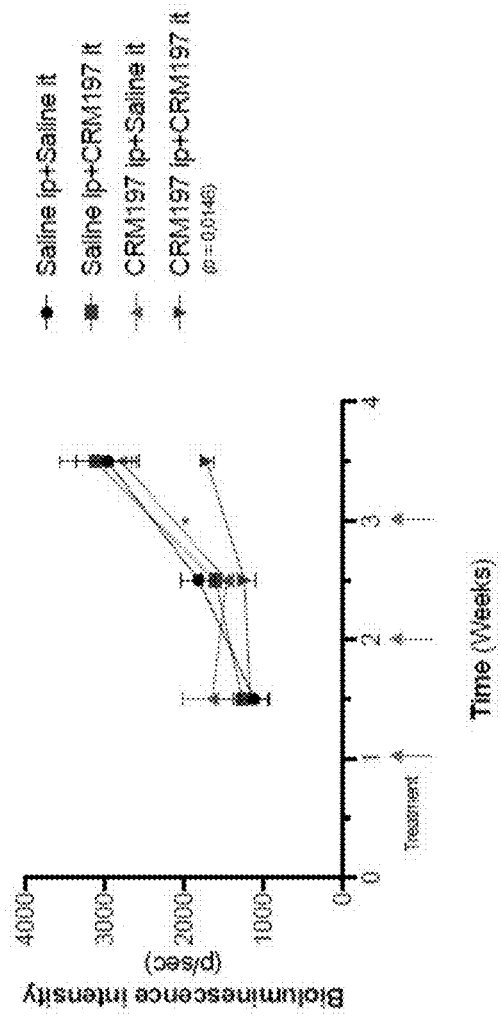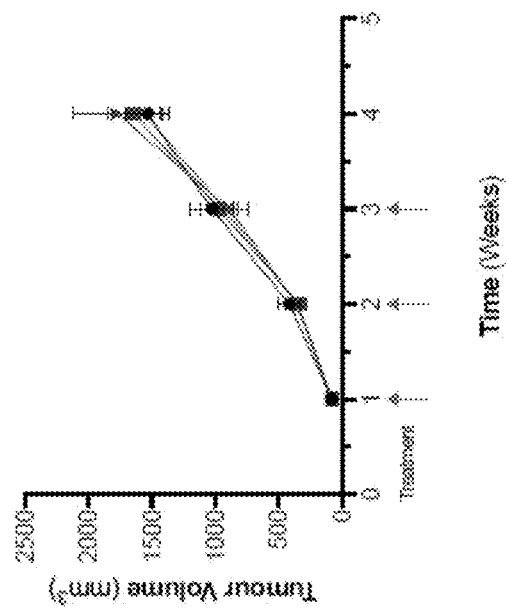

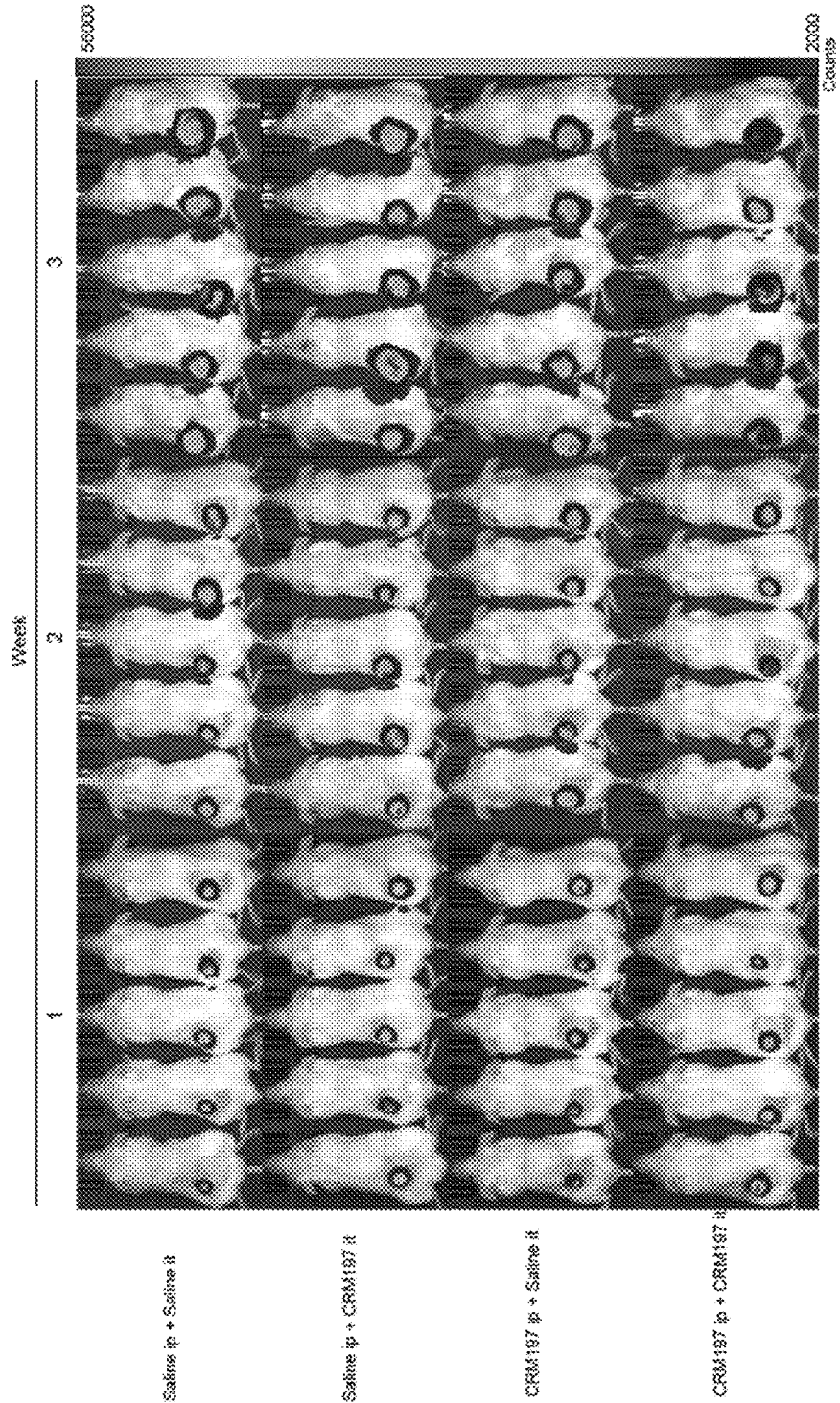

METHODS OF TUMOR VACCINATION

RELATED APPLICATIONS

This application claims priority to European Patent Application No. 19170999.7, filed Apr. 25, 2019, entitled "Pharmaceutical Combination", International PCT Application No. PCT/NL19/50451, filed Jul. 16, 2019, entitled "Pharmaceutical Combination", and U.S. Provisional Patent Application Ser. No. 62/961,554, filed Jan. 15, 2020, entitled "Methods of Tumor Vaccination". The entire disclosure of each of these applications is hereby incorporated herein by reference.

REFERENCE TO SEQUENCE LISTING SUBMITTED ELECTRONICALLY

The content of the electronically submitted sequence listing in ASCII text file (Name: 705550_DCP9-004B_ST25; Size: 7,844 bytes; and Date of Creation: Apr. 24, 2020) is incorporated herein by reference in its entirety.

BACKGROUND

Traditionally, and currently still, the focus in therapeutic tumor vaccines is on vaccination with tumor antigens, which are processed by antigen-presenting cells (APC's) such as dendritic cells (DCs) to thereby provide for T cell activation and the mounting of an immune response against the tumor.

The goal of such a vaccination strategy is to enlarge the pool of tumor-specific T-cells from the naïve repertoire, but also to reverse tumor-associated dormancy or anergy through the presentation of tumor antigens, in an effort to break central tolerance to those antigens and to overcome blunting of the $CD4^+$ and/or $CD8^+$ T cell repertoire.

The difficulty in designing therapeutic tumor vaccines, where preferentially T-cells against tumor-specific epitopes are stimulated, lies in the propensity of the tumor to evade immune control by altering itself to reduce expression of the tumor antigens or by creating an environment (the tumor micro-environment or TME) that is inhibitory for T cells and other cells of the immune system. In this way, T cell repertoires that recognize tumor antigens are inactivated, leading to inert or exhausted T cell populations.

Current vaccination approaches are dependent upon the tumor antigens expressed at a specific moment by the tumor. This means that these vaccination approaches are circumvented by the immune-evasive properties of tumor cells because the natural selection pressure on the tumor is generally not strong enough to force the tumor into cell death. Further, it remains difficult to employ tumor-specific antigens that are not also self-antigens, the latter being generally tolerized by the immune system or provide for weak T-cell-mediated immune responses. A current research focus in the field of therapeutic tumor vaccines lies in the identification of inter alia tumor neoantigens. Although these neoantigens might sufficiently stimulate T-cells following vaccination, they have an intrinsic disadvantage in that they are generally patient-specific and thus are not suitable as a tumor vaccine that finds broad application over the patient population. Also, they are not stably expressed and may alter over time, making it even more challenging to compose the correct vaccines formulations. It is clear from the above that current tumor vaccination approaches are based on vaccination with tumor antigens and are directed to the antigenic state of a tumor at a given time point, and thus do not actively manipulate the antigenic state of the tumor.

Accordingly, there is a need for improved therapeutic tumor vaccines and/or vaccination strategies, which are not dependent on tumor-antigen expressed by a tumor, and which incorporate antigens that provide for an optimal T-cell response upon vaccination. Such improved therapeutic tumor vaccines and/or vaccination strategies would be applicable in both human and veterinary use.

SUMMARY

A novel vaccination strategy, also referred to as 'tumor-antigen independent vaccination,' is provided herein. By designing a vaccination approach that is independent from tumor antigens, an immune response is raised against an antigen that is immunogenic in a subject (e.g., a human subject), wherein the antigen is of foreign (e.g., non-human) origin. Such an immunogen provides for a strong immune response, for instance by activating T-cells from the naïve repertoire or by tapping into pre-existing immunity by re-activating memory T-cells and/or memory B-cells that were generated during a prior immune response that was not an immune response against the tumor, and in some cases, was an immune response that occurred prior to establishment of a tumor as the result of common vaccination against infectious diseases. This principle overcomes the restrictions of tumor antigen-based vaccination methods described above and is applicable over the entire patient population. In addition, tumor-antigen independent vaccinations find value in animal healthcare, where readily targetable tumor antigens are poorly available, and where there is a high need for cost efficient immune therapies that are applicable across various species of animals.

In a first aspect, a vaccination strategy comprises administration (e.g., a vaccination step) of an immunogenic composition (e.g., a vaccine composition) comprising an antigen that is foreign or exogenous to a subject (e.g., a human subject) as an immunogen. In certain embodiments, the antigen is highly immunogenic, and can be an antigen that is not, or is only rarely, encountered by the immune system of the subject (e.g., a human subject) except via common vaccination against infectious diseases. In certain exemplary embodiments, a vaccination step is performed using a non-human antigen. In certain exemplary embodiments, a vaccination step is performed by using a non-tumor antigen.

In a second aspect, a vaccination strategy comprises actively marking a tumor cell (e.g., a tumor-marking step), or its direct or immediate environment (e.g., the tumor site or the tumor micro-environment (TME)) with the same antigen that was employed in the first aspect relating to vaccination. In certain exemplary embodiments, the tumor, or its direct environment (e.g., the tumor site or the tumor micro-environment (TME)) is manipulated by presentation of a non-tumor antigen (e.g., a non-human, non-tumor antigen). In certain exemplary embodiments, prior to tumor marking, such an immune response has already been elicited or mounted.

In certain exemplary embodiments, any antigen that is immunogenic in a subject (e.g., a human subject), that is of foreign (e.g., non-human) origin, and that is expected to provide a strong immune response, e.g., by activating T-cells from the naïve repertoire or by tapping into pre-existing immunity against antigens that are not antigens specific to the tumor of interest is used: (i) to vaccinate against said antigen so as to mount the desired immune response against said antigen; and (ii) to mark the tumor as a target for such an immune response by allowing presentation of a corresponding antigen at the tumor site or in the tumor micro-environment. The step of administering the immunogenic composition can be performed prior to or subsequent to tumor marking. In certain exemplary embodiments, one or more vaccination steps are performed prior to a tumor-marking step.

Accordingly, in certain aspects, a method for generating an immune response against a tumor in a subject comprising: a vaccination step comprising administering a first composition to the subject at a site distal to a tumor site, wherein the first composition comprises a non-tumor antigen or a nucleic acid encoding the non-tumor antigen; and a tumor-marking step comprising administering a second composition to the subject at the tumor site, wherein the second composition comprises the non-tumor antigen or a nucleic acid encoding the non-tumor antigen, wherein the time between the vaccination step and the tumor-marking step is between about one day and about 6 months, is provided.

In certain exemplary embodiments, the method further comprises one or more booster steps each comprising administering a booster composition to the subject, wherein the booster composition comprises the non-tumor antigen or a nucleic acid encoding the non-tumor antigen. In certain exemplary embodiments, the one or more booster steps occur prior to the tumor-marking step.

In certain exemplary embodiments, the tumor marking-step comprises administering the second composition into the tumor or proximal to the tumor.

In certain exemplary embodiments, the vaccination step comprises administering the first composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain exemplary embodiments, the vaccination step comprises intradermally administering the first composition. In certain exemplary embodiments, the first composition is prepared for intradermal injection. In certain exemplary embodiments, the first composition comprises a diluent or solvent acceptable for intradermal injection. In certain exemplary embodiments, the vaccination step comprises intramuscularly administering the first composition. In certain exemplary embodiments, the first composition is prepared for intramuscular injection. In certain exemplary embodiments, the first composition comprises a diluent or solvent acceptable for intramuscular injection.

In certain exemplary embodiments, the vaccination step comprises administering the first composition into an organ system that is different than the organ system in which the tumor resides. In certain exemplary embodiments, the vaccination step comprises administering the first composition at a site contralateral to the tumor.

In certain exemplary embodiments, the vaccination step is performed subsequent to the tumor-marking step. In certain exemplary embodiments, the tumor-marking step is performed subsequent to the vaccination step. In certain exemplary embodiments, the time between the vaccination step and the tumor-marking step is sufficient for an immune response to be mounted as a result of the vaccination step. In certain exemplary embodiments, the time between the vaccination step and the tumor-marking step is about 2 days to about 21 days.

In certain exemplary embodiments, the tumor is a solid tumor. In certain exemplary embodiments, the solid tumor is glioblastoma or ovarian cancer.

In certain exemplary embodiments, the first composition comprises a dendritic cell comprising the non-tumor antigen or a nucleic acid encoding the non-tumor antigen. In certain exemplary embodiments, the dendritic cell is a CD34-positive, CD1a-positive, and CD83-positive mature dendritic cell. In certain exemplary embodiments, the mature dendritic cell is derived from DCOne.

In certain exemplary embodiments, the second composition is prepared for intratumoral administration. In certain exemplary embodiments, the second composition comprises a tumor targeting component. In certain exemplary embodiments, the tumor targeting component is a tumor-specific virus. In certain exemplary embodiments, the tumor-specific virus is an oncolytic virus. In certain exemplary embodiments, the tumor-specific virus comprises the non-tumor antigen or a nucleic acid encoding the non-tumor antigen. In certain exemplary embodiments, the tumor targeting component is a tumor-specific nanoparticle. In certain exemplary embodiments, the tumor-specific nanoparticle comprises the non-tumor antigen or a nucleic acid encoding the non-tumor antigen.

In certain exemplary embodiments, the second composition comprises a dendritic cell comprising the non-tumor antigen or a nucleic acid encoding the non-tumor antigen. In certain exemplary embodiments, the dendritic cell is a CD34-positive, CD1a-positive, and CD83-positive mature dendritic cell. In certain exemplary embodiments, the mature dendritic cell is derived from DCOne.

In certain exemplary embodiments, the first and second compositions each optionally comprises one or more pharmaceutically-acceptable carriers, adjuvants, excipients and/or diluents.

In certain exemplary embodiments, the subject is a non-tumor antigen-naïve subject. In certain exemplary embodiments, the subject has previously been exposed to the non-tumor antigen. In certain exemplary embodiments, the subject has previously mounted an immune response against the non-tumor antigen.

In certain exemplary embodiments, the subject is a human. In certain exemplary embodiments, the subject is a domesticated animal and/or an animal suitable for veterinary healthcare.

In other aspects, a method for generating an immune response against a tumor in a subject comprising: a vaccination step comprising administering a first composition to the subject at a site distal to a tumor site, wherein the first composition comprises a non-tumor recall antigen or a nucleic acid encoding the non-tumor recall antigen; and a tumor-marking step comprising administering a second composition to the subject at the tumor site, wherein the second composition comprises the recall antigen or a nucleic acid encoding the recall antigen, is provided.

In certain exemplary embodiments, the tumor marking-step comprises administering the second composition into the tumor or proximal to the tumor.

In certain exemplary embodiments, the vaccination step comprises administering the first composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain exemplary embodiments, the vaccination step comprises intradermally administering the first composition. In certain exemplary embodiments, the first composition is prepared for intradermal injection. In certain exemplary embodiments, the first composition comprises a diluent or solvent acceptable for intradermal injection. In certain exemplary embodiments, the vaccination step comprises intramuscularly administering the first composition.

In certain exemplary embodiments, the first composition is prepared for intramuscular injection. In certain exemplary embodiments, the first composition comprises a diluent or solvent acceptable for intramuscular injection.

In certain exemplary embodiments, the vaccination step comprises administering the first composition into an organ system that is different than the organ system in which the tumor resides. In certain exemplary embodiments, the vaccination step comprises administering the first composition at a site contralateral to the tumor.

In certain exemplary embodiments, the vaccination step and the tumor-marking step are temporally separated. In certain exemplary embodiments, the vaccination step is performed subsequent to the tumor-marking step. In certain exemplary embodiments, the tumor-marking step is performed subsequent to the vaccination step. In certain exemplary embodiments, the time between the vaccination step and the tumor-marking step is sufficient for an immune response to be mounted as a result of the vaccination step. In certain exemplary embodiments, the time between the vaccination step and the tumor-marking step is about 2 days to about 21 days.

In certain exemplary embodiments, the tumor is a solid tumor. In certain exemplary embodiments, the solid tumor is glioblastoma or ovarian cancer.

In certain exemplary embodiments, the first composition comprises a dendritic cell comprising the recall antigen or a nucleic acid encoding the recall antigen. In certain exemplary embodiments, the dendritic cell is a CD34-positive, CD1a-positive, and CD83-positive mature dendritic cell. In certain exemplary embodiments, the mature dendritic cell is derived from DCOne.

In certain exemplary embodiments, the second composition is prepared for intratumoral administration. In certain exemplary embodiments, the second composition comprises a tumor targeting component. In certain exemplary embodiments, the tumor targeting component is a tumor-specific virus. In certain exemplary embodiments, the tumor-specific virus is an oncolytic virus. In certain exemplary embodiments, the tumor-specific virus comprises the recall antigen or a nucleic acid encoding the recall antigen. In certain exemplary embodiments, the tumor targeting component is a tumor-specific nanoparticle. In certain exemplary embodiments, the tumor-specific nanoparticle comprises the recall antigen or a nucleic acid encoding the recall antigen.

In certain exemplary embodiments, the second composition comprises a dendritic cell comprising the recall antigen or a nucleic acid encoding the recall antigen. In certain exemplary embodiments, the dendritic cell is a CD34-positive, CD1a-positive, and CD83-positive mature dendritic cell. In certain exemplary embodiments, the mature dendritic cell is derived from DCOne.

In certain exemplary embodiments, the first and second compositions each optionally comprises one or more pharmaceutically-acceptable carriers, adjuvants, excipients and/or diluents.

In certain exemplary embodiments, the subject has previously been exposed to the recall antigen. In certain exemplary embodiments, the subject has previously mounted an immune response against the recall antigen.

In certain exemplary embodiments, the subject is a human. In certain exemplary embodiments, the subject is a domesticated animal and/or an animal suitable for veterinary healthcare.

In other aspects, a method for generating an immune response against a tumor in a subject comprising: a vaccination step comprising administering a first composition to the subject at a site distal to a tumor site, wherein the first composition comprises a diphtheria toxin or detoxified variant thereof or a nucleic acid encoding the diphtheria toxin or detoxified variant thereof; and a tumor-marking step comprising administering a second composition to the subject at the tumor site, wherein the second composition comprises a diphtheria toxin or detoxified variant thereof or a nucleic acid encoding the diphtheria toxin or detoxified variant thereof, is provided.

In certain exemplary embodiments, the method further comprises one or more booster steps each comprising administering a booster composition to the subject, wherein the booster composition comprises the diphtheria toxin or detoxified variant thereof or a nucleic acid encoding the diphtheria toxin or detoxified variant thereof. In certain exemplary embodiments, the one or more booster steps occur prior to the tumor-marking step.

In certain exemplary embodiments, the diphtheria toxin or detoxified variant thereof is CRM197.

In certain exemplary embodiments, the tumor marking-step comprises administering the second composition into the tumor or proximal to the tumor.

In certain exemplary embodiments, the vaccination step comprises administering the first composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue. In certain exemplary embodiments, the vaccination step comprises intradermally administering the first composition. In certain exemplary embodiments, he first composition is prepared for intradermal injection. In certain exemplary embodiments, the first composition comprises a diluent or solvent acceptable for intradermal injection. In certain exemplary embodiments, the vaccination step comprises intramuscularly administering the first composition. In certain exemplary embodiments, the first composition is prepared for intramuscular injection. In certain exemplary embodiments, the first composition comprises a diluent or solvent acceptable for intramuscular injection.

In certain exemplary embodiments, the vaccination step comprises administering the first composition into an organ system that is different to the organ system in which the tumor resides. In certain exemplary embodiments, the vaccination step comprises administering the first composition at a site contralateral to the tumor.

In certain exemplary embodiments, the vaccination step and the tumor-marking step are temporally separated. In certain exemplary embodiments, the vaccination step is performed subsequent to the tumor-marking step. In certain exemplary embodiments, the tumor-marking step is performed subsequent to the vaccination step. In certain exemplary embodiments, the time between the vaccination step and the tumor-marking step is sufficient for an immune response to be mounted as a result of the vaccination step. In certain exemplary embodiments, the time between the vaccination step and the tumor-marking step is about 2 days to about 21 days.

In certain exemplary embodiments, the tumor is a solid tumor. In certain exemplary embodiments, the solid tumor is glioblastoma or ovarian cancer.

In certain exemplary embodiments, the first composition comprises a dendritic cell comprising CRM197 or a nucleic acid encoding CRM197. In certain exemplary embodiments, the dendritic cell is a CD34-positive, CD1a-positive, and CD83-positive mature dendritic cell. In certain exemplary embodiments, the mature dendritic cell is derived from DCOne.

In certain exemplary embodiments, the second composition is prepared for intratumoral administration. In certain exemplary embodiments, the second composition comprises a tumor targeting component. In certain exemplary embodiments, the tumor targeting component is a tumor-specific virus. In certain exemplary embodiments, the tumor-specific virus is an oncolytic virus. In certain exemplary embodiments, the tumor-specific virus comprises CRM197 or a nucleic acid encoding CRM197. In certain exemplary embodiments, the tumor targeting component is a tumor-specific nanoparticle. In certain exemplary embodiments, the tumor-specific nanoparticle comprises CRM197 or a nucleic acid encoding CRM197.

In certain exemplary embodiments, the second composition comprises a dendritic cell comprising CRM197 or a nucleic acid encoding CRM197. In certain exemplary embodiments, the dendritic cell is a CD34-positive, CD1a-positive, and CD83-positive mature dendritic cell. In certain exemplary embodiments, the mature dendritic cell is derived from DCOne.

In certain exemplary embodiments, the first and second compositions each optionally comprises one or more pharmaceutically-acceptable carriers, adjuvants, excipients and/or diluents.

In certain exemplary embodiments, the subject is a human. In certain exemplary embodiments, the subject is a domesticated animal and/or an animal suitable for veterinary healthcare.

In other aspects, a method for generating an immune response against a tumor in a subject, comprising administering to the subject a non-tumor antigen or a nucleic acid encoding the non-tumor antigen at a tumor site, wherein the subject is previously vaccinated with the non-tumor antigen or a nucleic acid encoding the non-tumor antigen, is provided.

In other aspects, a method for generating an immune response against a tumor in a subject, comprising administering to the subject a recall antigen or a nucleic acid encoding the recall antigen at a tumor site, wherein the subject is previously vaccinated with the antigen or a nucleic acid encoding the antigen, and wherein the antigen is a non-tumor antigen, is provided.

In other aspects, a method for generating an immune response against a tumor in a subject, comprising administering to the subject a diphtheria toxin or detoxified variant thereof or a nucleic acid encoding the diphtheria toxin or detoxified variant thereof at a tumor site, wherein the subject is previously vaccinated with the diphtheria toxin or detoxified variant thereof or the nucleic acid encoding the diphtheria toxin or detoxified variant thereof, is provided.

In certain exemplary embodiments, the diphtheria toxin or detoxified variant thereof is CRM197.

BRIEF DESCRIPTION OF THE DRAWINGS

FIG. 4A-FIG. 4B depict tumor growth inhibition in a humanized U87-MG glioblastoma model. Tumor size was monitored three times per week using a digital caliper (FIG. 4A). Tumor size at day 18 in vaccinated mice injected as indicated is shown in FIG. 4B.

FIG. 6A-FIG. 6D depict anti-KLH IgG (FIGS. 6C-6D) and IgM (FIGS. 6A-6B) levels in the serum of mice over time. Anti-KLH IgM and anti-KLH IgM concentrations (Ul/mL) were measured by ELISA using the sera of mice taken at D0, D14 and at sacrifice. N=5 mice per group. Graphs represent the individual data of anti-KLH IgG and IgM per group ((FIG. 6A and FIG. 6C) is the glioblastoma group, (FIG. 6B and FIG. 6D) is the melanoma group). Two-way ANOVA with Dunnet's multiple comparison test was used. * vs vehicle group, *<0.05, <0.01, *<0.001, ****<0.0001).

FIG. 8A-FIG. 8B depict tumor growth in a humanized OV90luc ovarian cancer mouse model. Tumor volumes (in $mm^3$) were calculated by the ellipsoid formula $(L \times W \times H)\pi/6$ (FIG. 8A). Bioluminescence intensity (photons/sec) is depicted (FIG. 8B).

FIG. 9 depicts imaging data showing bioluminescence intensity (total photon flux (Optical) per animal) over time.

DETAILED DESCRIPTION

Figure 1B:
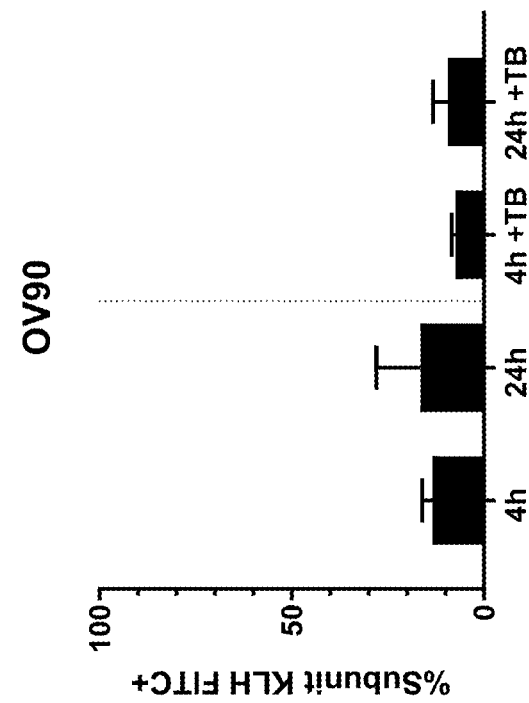
FIG. 1A-FIG. 1B depict the uptake of subunit KLH protein by DCOne mDC cells (n=3) (FIG. 1A) and the labelling of OV90 ovarian cancer cells (n=2) (FIG. 1B) after 4 hours and 24 hours. 0.08% trypan blue (TB) was added to quench extracellular bound subunit KLH-FITC to visualize the percentage intracellular subunit KLH-FITC.

Provided herein are methods for generating an immune response against a tumor in a subject. The methods generally comprise a vaccination step comprising administering a first composition to a subject at a site distal to a tumor site, wherein the first composition comprises a non-tumor antigen or a nucleic acid encoding the non-tumor antigen, and a tumor-marking step comprising administering a second composition to the subject at the tumor site, wherein the second composition comprises the same non-tumor antigen (or nucleic acid encoding the same non-tumor antigen).

The term "immune response," as used herein, includes T-cell mediated and/or B-cell mediated immune responses. Exemplary immune functions of T cells include, e.g., cytokine production and induction of cytotoxicity in other cells. B-cell functions include antibody production. In addition, the term includes immune responses that are indirectly affected by T-cell activation, e.g., antibody production and activation of cytokine responsive cells, e.g., macrophages. Immune cells involved in the immune response include lymphocytes, such as B cells and T cells ($CD4^+$ and $CD8^+$ cells); antigen presenting cells (e.g., professional antigen presenting cells such as dendritic cells, macrophages, B lymphocytes, Langerhans cells, and non-professional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In certain embodiments, the term refers to a T-cell mediated immune response. The immune response may in some embodiments be a T cell-dependent immune response. The skilled person understands that the phrase "immune response against a tumor" also includes immune responses against a non-human antigenic polypeptide that is introduced into the tumor micro-environment by intratumoral administration, such as intratumoral administration of (i) dendritic cells, including autologous or allogeneic dendritic cells, loaded with said polypeptide or (ii) viruses comprising a nucleic acid encoding said polypeptide.

The term "T-cell dependent immune response," as used herein, refers to an immune response wherein either T-cells, B-cells or both T- and B-cell populations are activated, and wherein T-cells further assist T and B cells and other immune cells in executing their function.

The term "tumor," as used herein, includes reference to cellular material, e.g., a tissue, proliferating at an abnormally high rate. A growth comprising neoplastic cells is a neoplasm, also known as a "tumor," and generally forms a distinct tissue mass in a body of a subject. A tumor may show partial or total lack of structural organization and functional coordination with the normal tissue. As used herein, a tumor is intended to encompass hematopoietic tumors as well as solid tumors. In certain embodiments, the tumor is a solid tumor. The term "tumor," as used herein, includes reference to the tumor micro-environment or tumor site, i.e., the area within the tumor and the area directly outside the tumorous tissue. In certain embodiments, the tumor micro-environment or tumor site includes an area within the boundaries of the tumor tissue. In certain embodiments, the tumor micro-environment or tumor site includes the tumor interstitial compartment of a tumor, which is defined herein as all that is interposed between the plasma membrane of neoplastic cells and the vascular wall of the newly formed neovessels. As used herein, the terms "tumor micro-environment" or "tumor site" refers to a location within a subject in which a tumor resides, including the area immediately surrounding the tumor.

A tumor may be benign (e.g., a benign tumor) or malignant (e.g., a malignant tumor or cancer). Malignant tumors can be broadly classified into three major types: those arising from epithelial structures are called carcinomas, those that originate from connective tissues such as muscle, cartilage, fat or bone are called sarcomas, and those affecting hematopoietic structures (structures pertaining to the formation of blood cells) including components of the immune system, are called leukemias and lymphomas. Other tumors include, but are not limited to, neurofibromatosis. In certain exemplary embodiments, the tumor is a glioblastoma. In certain exemplary embodiments, the tumor is an ovarian cancer (e.g., an epithelial ovarian cancer, which can be further subtyped into a serous, a clear cell, an endometrioid, a mucinous, or a mixed epithelial ovarian cancer).

Solid tumors are abnormal masses of tissue that can be benign or malignant. In certain embodiments, solid tumors are named for the type of cells that form them (such as sarcomas, carcinomas, and lymphomas). Examples of solid tumors, such as sarcomas and carcinomas, include, but are not limited to, liposarcoma, fibrosarcoma, chondrosarcoma, osteosarcoma, myxosarcoma, and other sarcomas, mesothelioma, synovioma, leiomyosarcoma, Ewing's tumor, colon carcinoma, rhabdomyosarcoma, pancreatic cancer, lymphoid malignancy, lung cancers, breast cancer, prostate cancer, ovarian cancer, hepatocellular carcinoma, adenocarcinoma, basal cell carcinoma, sweat gland carcinoma, squamous cell carcinoma, medullary thyroid carcinoma, pheochromocytomas sebaceous gland carcinoma, papillary thyroid carcinoma, papillary adenocarcinomas, papillary carcinoma, medullary carcinoma, bronchogenic carcinoma, hepatoma, renal cell carcinoma, bile duct carcinoma, Wilms' tumor, choriocarcinoma, cervical cancer, seminoma, testicular tumor, bladder carcinoma, melanoma, CNS tumors (e.g., a glioma, e.g., brainstem glioma and mixed gliomas, glioblastoma (e.g., glioblastoma multiforme), germinoma, astrocytoma, craniopharyngioma, medulloblastoma, ependymoma, Schwannoma, CNS lymphoma, acoustic neuroma, pinealoma, hemangioblastoma, meningioma, oligodendroglioma, retinoblastoma, neuroblastoma, and brain metastases), and the like.

Carcinomas that can be amenable to therapy by a method disclosed herein include, but are not limited to, squamous cell carcinoma (various tissues), basal cell carcinoma (a form of skin cancer), esophageal carcinoma, bladder carcinoma, including transitional cell carcinoma (a malignant neoplasm of the bladder), hepatocellular carcinoma, colorectal carcinoma, bronchogenic carcinoma, lung carcinoma, including small cell carcinoma and non-small cell carcinoma of the lung, colon carcinoma, thyroid carcinoma, gastric carcinoma, breast carcinoma, ovarian carcinoma, adrenocortical carcinoma, pancreatic carcinoma, sweat gland carcinoma, prostate carcinoma, papillary carcinoma, adenocarcinoma, sebaceous gland carcinoma, medullary carcinoma, papillary adenocarcinoma, ductal carcinoma in situ or bile duct carcinoma, cystadenocarcinoma, renal cell carcinoma, choriocarcinoma, Wilm's tumor, seminoma, embryonal carcinoma, cervical carcinoma, testicular carcinoma, nasopharyngeal carcinoma, osteogenic carcinoma, epithelial carcinoma, uterine carcinoma, and the like.

Sarcomas that can be amenable to therapy by a method disclosed herein include, but are not limited to, myxosarcoma, chondrosarcoma, chordoma, osteogenic sarcoma, liposarcoma, fibrosarcoma, angiosarcoma, lymphangiosarcoma, endotheliosarcoma, osteosarcoma, mesothelioma, Ewing's sarcoma, leiomyosarcoma, rhabdomyosarcoma, lymphangioendotheliosarcoma, synovioma, and other soft tissue sarcomas.

The term "subject," as used herein, refers to the recipient of a method as described herein, i.e., a recipient that can mount a cellular immune response, and is a mammal. In certain embodiments, the subject is a human. In certain embodiments, the subject is a domesticated animal, e.g., a horse, a cow, a pig, a sheep, a dog, a cat, etc. In certain embodiments, the subject is an animal suitable for veterinary healthcare, e.g., a zoo animal. The terms "patient" and "subject" may be used interchangeably. In certain embodiments, the subject is a human suffering from a tumor (e.g., a solid tumor). In certain embodiments, the subject is a domesticated animal suffering from a tumor (e.g., a solid tumor). In certain embodiments, the subject is an animal suitable for veterinary healthcare suffering from a tumor (e.g., a solid tumor). As used herein, an "animal suitable for veterinary healthcare" is any animal that is suitable for treatment by a veterinarian, and includes, without limitation, wild animals, domesticated animals, and zoo animals that are capable of mounting a cellular immune response.

The term "polypeptide," as used herein, refers to a molecule composed of amino acid monomers linearly linked by amide bonds (peptide bonds). As used herein, the term is mutually inclusive of the terms "peptide" and "protein" and includes reference to parts of said polypeptides.

The term "nucleic acid," as used herein, refers to DNA and RNA including mRNA or cDNA, as well as synthetic congeners thereof. The nucleic acid can be a recombinant or synthetic nucleic acid.

The term "antigen" or "antigenic," as used in relation to a polypeptide as described herein, refers generally to a biological molecule which contains at least one epitope specifically recognized by a T-cell receptor, an antibody, or other elements of specific humoral and/or cellular immunity. The whole molecule may be recognized, or one or more portions of the molecule, for instance following intracellular processing of a polypeptide into an MHC peptide antigen complex and subsequent antigen presentation. The term "antigenic polypeptide" is interchangeable with "polypeptide antigen." This terminology includes antigenic parts of said polypeptides, for instance produced after intracellular processing of a polypeptide and in the context of a MHC peptide antigen complex. The term "antigen" or "antigenic" includes reference to at least one, or more, antigenic epitopes of a polypeptide as described herein. In certain embodiments, a "non-tumor antigen" refers to herein as an antigen that is not derived from a tumor. For example, in certain embodiments, a non-tumor antigen may be a foreign antigen. In certain exemplary embodiments, a non-tumor antigen may be a bacterial toxin, e.g., a non-toxic variant of diphtheria toxin.

The term "antigen" or "antigenic" may also be used to refer to a polypeptide that includes modifications, such as deletions, additions and substitutions to the native sequence, as long as the polypeptide maintains the ability to be specifically recognized by T-cell receptors and/or antibodies following vaccination with said polypeptide as an immunogen. These modifications may be deliberate, as through site-directed mutagenesis, or through particular synthetic procedures, or through a genetic engineering approach, or may be accidental, such as through mutations of hosts, which produce the antigens. Synthetic antigens are also included, for example, polyepitopes, flanking epitopes, and other recombinant or synthetically derived antigens (Bergmann et al. (1993) *Eur. J. Immunol.* 23:2777 2781; Bergmann et al. (1996) *J. Immunol.* 157:3242 3249; Suhrbier, A. (1997) Immunol. and Cell Biol. 75:402 408; Gardner et al. (1998) 12th World AIDS Conference, Geneva, Switzerland, Jun. 28-Jul. 3, 1998, the disclosures of which are incorporated by reference herein in their entireties). In certain embodiments, the antigenic polypeptide contains at least 1, 2, 3, 4, 5, 6, 7, 8, 9 or 10 $CD4^+$ T-helper cell epitope(s) and/or at least 1, 2, 3, 4, 5, 6, 7, 8, 9 or 10 $CD8^+$ cytotoxic T-cell epitope(s).

The term "immunogenic composition," as used herein, refers to a substance which induces a specific immune response against an immunogen in a subject who is in need of an immune response against said immunogen. The composition may include an adjuvant and optionally one or more pharmaceutically-acceptable carriers, excipients and/or diluents. The immunogenic composition can be employed in prime-boost vaccination, such as at least 2, 3, 4 or at least 5 immunizations separated in time. The immunogenic composition can be an (allogeneic) dendritic cell comprising said immunogen.

The term "immunogen," as used herein, refers to a compound such as a polypeptide capable of eliciting an immune response that is specifically directed against an antigenic polypeptide as described herein. An immunogen is also an antigen, i.e., an antigenic polypeptide. In contrast, an antigen is not necessarily an immunogen. In certain embodiments, the immunogen is used for vaccination (in an immunogenic composition such as a vaccine composition), and the antigenic polypeptide prepared for intratumoral delivery is instead used for marking a tumor as a target for an immune response to be elicited, or as a target for an immune response that is already elicited, in a subject. The term "immunogen" is also used to refer to a nucleic acid which encodes the non-human antigenic polypeptide as described herein. In addition, embodiments that describe the antigenic polypeptide, also apply to an immunogen as described herein.

The term "non-human," as used herein in the context of an antigenic polypeptide, includes polypeptides that are not of human origin, including a bacterial polypeptide, a polypeptide of an organism of the Archaea domain, a fungal polypeptide and a viral polypeptide. Also included are plant polypeptides and non-human mammalian polypeptides such as polypeptides of non-human primates, rodents (e.g., mice and rats), rabbits, pigs, sheep, goats, cows, pigs, horses and donkeys, and birds (e.g., chickens, turkeys, ducks, geese and the like). Also included are polypeptides of snails or other mollusks, including *Megathura crenulata*. The term "non-human" also encompasses synthetic polypeptides, i.e., polypeptides that have an artificial sequence designed by man and that do not occur in nature or are not yet identified in nature. In addition, the term comprises human polypeptides comprising an amino acid alteration from the native sequence, the alteration providing for immunogenicity in a human subject.

The term "intratumoral," as used herein, refers to delivery or transport of the antigenic polypeptide, or the nucleic acid encoding said polypeptide, into a tumor. One example of intratumoral delivery, or transport, of an antigenic polypeptide as described herein is by intratumoral administration, a route of administration generally known in the art. As an alternative route for intratumoral administration, the antigen may be delivered to the tumor via a tumor-specific carrier, such as an oncolytic virus or a gene therapy vector, which have been broadly developed to deliver gene sequences to tumors. The use of such vehicles allows for multiple routes of administration, in addition to intratumoral administration, such by as intravenous or intraperitoneal administration, subsequently resulting in the delivery of the nucleic acid encoding said polypeptide, into the tumor (Lundstrom, *Diseases,* 6(2):42 (2018); Alemany, *Biomedicines,* 2, p. 36-49 (2014); Twumasi-Boateng et al., *Nature Reviews Cancer* 18, p. 419-432 (2018), the disclosures of which are incorporated by reference herein in their entireties).

The phrase "prepared for intratumoral delivery," as used herein, refers to an antigenic polypeptide as described herein, or a nucleic acid encoding said polypeptide as described herein, that is adapted for intratumoral delivery and/or is in a formulation that allows for intratumoral delivery. The preparation used for intratumoral delivery may be composed such that it has a beneficial effect on the interaction between the immune system and the tumor. For instance, dendritic cells, such as autologous or allogeneic dendritic cells, can be loaded with said polypeptide and upon intratumoral administration may provide for additional immune stimulation via direct interaction with T cells entering the tumor and/or indirectly by recruiting bystander antigen-presenting cells (Laurell et al., *Journal for Immunotherapy of Cancer,* 5:52 (2017); Wallgren et al., *Scandinavian Journal of Immunology,* 62, p. 234-242 (2005), the disclosures of which are incorporated by reference herein in their entireties). Another example of such preparation is that the polypeptide or nucleic acid as described herein can be comprised in a tumor-delivery vehicle such as a tumor-targeted vehicle including a tumor-specific virus such as an oncolytic virus (or any other virus that selectively replicates in tumor cells) that infects a tumor cell and which allows for (i) expression of said nucleic acid in a tumor cell, and (ii) (subsequently) intracellular processing and antigen presentation (MHC) of said (expressed) polypeptide by said tumor cell. The skilled person is well aware of other methods and means for preparing a polypeptide, or a nucleic acid encoding said polypeptide, for intratumoral delivery. For instance, the skilled person can apply other tumor-targeted delivery vehicles such as a tumor-specific nanoparticle or he can apply intratumoral administration through intratumoral injection in order to deliver said polypeptide or nucleic acid into a tumor. In certain embodiments, the polypeptide or nucleic acid prepared for intratumoral delivery as described herein, is comprised in a tumor-targeted vehicle.

As used herein, the term "extratumoral" refers to a location, e.g., in the body of a subject, that is away (e.g., distal) from a tumor and immediately surrounding tissue (e.g., that may make up the tumor micro-environment).

The compositions for use as described herein, elicit an immune response specifically directed against a tumor in a subject. The skilled person understands that "specifically directed" refers to an immune response that is specific for a tumor. The specificity is introduced by a step of marking a tumor with a non-human antigenic polypeptide as a target for an immune response, and by eliciting an immune response against an antigenic part of said non-human antigenic polypeptide (i.e., the target). Thus, In certain embodiments, the compositions for use as described herein, is for use in eliciting an immune response against a tumor marked as a target for said immune response. In certain embodiments, the compositions for use as described herein, is for use in eliciting an immune response against a tumor that is marked as a target for said immune response; wherein said target is a non-human antigenic polypeptide as described herein.

In certain embodiments, the non-human antigenic polypeptide, or a nucleic acid encoding said polypeptide, prepared for intratumoral delivery as described herein, serves the purpose of marking the tumor as a target for an immune response (polypeptide/nucleic acid for marking a tumor). Thus, In certain embodiments, said polypeptide or said nucleic acid prepared for intratumoral delivery marks the tumor as a target for an immune response following intratumoral delivery.

As used herein, the term "vaccination step" refers to a step in a method (vaccination strategy) as described herein, wherein a composition comprising an antigenic polypeptide (e.g., a non-tumor antigen) or a nucleic acid encoding an antigenic polypeptide is administered to a subject at a site distal to a tumor site. In certain embodiments, in a vaccination step of a method as described herein, the composition is administered at a site that is not the site in which the tumor resides (e.g., not the tumor site). In certain embodiments, in a vaccination step of a method as described herein, the composition is administered at an extratumoral site.

As used herein, the term "booster step" refers to a step in a method (vaccination strategy) as described herein, wherein a booster composition comprising an antigenic polypeptide (e.g., a non-tumor antigen) or a nucleic acid encoding the antigenic polypeptide is administered to a subject at a site distal to a tumor site. In certain embodiments, a booster step is performed after a vaccination step, wherein the vaccination step results in an immune response against the antigen, and the booster step enhances the immune response against the antigen. In certain embodiments, a booster step results in an enhanced immune response in a subject having pre-existing immunity against, e.g., an antigenic polypeptide (e.g., a non-tumor antigen). In certain embodiments, the vaccination step in a method as described herein is a booster stem, e.g., when the subject has pre-existing immunity against, e.g., a non-tumor recall antigen.

The term "marking," "mark" or "marked," as used herein, refers to active manipulation of the antigenic state of a tumor by intratumoral delivery of an antigenic polypeptide, or a nucleic acid encoding said polypeptide, as described herein. This provides for direct labelling of a tumor cell through intracellular delivery and subsequent processing and presentation of said polypeptide by said tumor cell, or provides for indirect labelling of a tumor via: (i) intracellular delivery and subsequent processing and presentation of said polypeptide by a non-tumor cell in said tumor; or (ii) extracellular delivery of said antigenic polypeptide to said tumor (i.e., extracellular to the cells present in said tumor before marking), for instance by using a dendritic cell that comprises a nucleic acid encoding said polypeptide or that is loaded with said antigenic polypeptide. As used herein, the term "tumor-marking step" refers to a step in a method (e.g., a vaccination strategy) as described herein, wherein a composition comprising an antigenic polypeptide (e.g., a non-tumor antigen) or a nucleic acid encoding an antigenic polypeptide is administered to a subject at a tumor site. In certain exemplary embodiments, the tumor-marking step comprises the use of compositions, methods or technologies which facilitate the delivery of antigens into the cytosol of tumor cells.

The immunogenic composition as described herein, which also comprises said non-human antigenic polypeptide or a nucleic acid encoding said polypeptide, but as an immunogen (polypeptide/nucleic acid for eliciting an immune response), serves the purpose of eliciting an immune response against a tumor that is marked, or to be marked, with said non-human antigenic polypeptide. Thus, in certain embodiments, said immunogen is used to elicit an immune response against a tumor that is marked, or is to be marked, with said non-human antigenic polypeptide, or a nucleic acid encoding said antigenic polypeptide, prepared for intratumoral delivery. In principle, any antigenic polypeptide can be introduced into a tumor to generate a new antigenic target. In certain embodiments, any antigenic polypeptide can be introduced into a tumor to generate new antigenic target that is a B-cell epitope and/or T-cell epitope recognizable by an antibody and/or T-cell receptor, respectively, when an immune response against said target is elicited following administration of an immunological composition as described herein to a subject.

The skilled person directly understands that: (i) the non-human antigenic polypeptide, or a nucleic acid encoding said polypeptide, prepared for intratumoral delivery as described herein (polypeptide/nucleic acid for marking a tumor); and (ii) the non-human antigenic polypeptide, or a nucleic acid encoding said polypeptide, comprised as an immunogen in an immunogenic composition as described herein (polypeptide/nucleic acid for eliciting an immune response), are matched in that the immunogen, when administered, elicits an immune response that is directed against one or more (target) epitopes established by the polypeptide or nucleic acid for marking the tumor.

Thus, for instance, the polypeptides under (i) and (ii) are immunologically matched in that a T-cell epitope and/or a B-cell epitope of the marking polypeptide in a tumor are recognized by, or are reactive with, a T-cell and/or B-cell response elicited by the polypeptide employed as an immunogen. It is thus understood that the polypeptides under (i) and (ii) are based on the same non-human antigenic polypeptide and optionally share an identical antigenic part thereof, optionally at least one B-cell and/or T-cell epitope thereof (i.e., are immunologically matched). In this manner, the elicited immune response is specifically directed to the tumor marked as a target for said immune response. Thus, the formulations of the said polypeptide used for eliciting an immune response on the one hand and tumor marking on the other hand need not be the same. In fact, the skilled person appreciates that it might be beneficial to use different formulations of the said polypeptide for vaccination and tumor marking.

The term "T-cell mediated immune response," as used herein, refers to an immune response that is T-cell driven, and where elicitation of another or further immune response is dependent on activation of T-cells. In certain embodiments, the immune response is a T-cell mediated immune response/T-cell dependent immune response. The skilled person is well aware of methods and means for mounting a T-cell mediated immune response/T-cell dependent immune response, for instance through selection of an appropriate antigen of which many have been described in literature including but not limited to bacterial-, fungal-, mollusk-, snail-, insect- or plant-derived antigens to which measurable T cell responses have been documented, or by selecting an appropriate adjuvant or carrier such as a chemical adjuvant, biological adjuvant, protein, viral vaccine, dendritic cell vaccine or any other composition that can be administered as a vaccine composition (Bender et al., *J. Exp. Med,* 182: 1663-1671 (1995); Bennett et al., *Nature,* 393:478-480 (1998); Kalinski and Moser, *Nature,* 5:251-260 (2005); Pashine et al., *Nature Medicine Supplement,* 11:S63-S68 (2005), the disclosures of which are incorporated by reference herein in their entireties).

The term "tumor-specific virus," as used herein, includes reference to any virus that has the capacity to selectively replicate in tumor cells.

The term "oncolytic virus," as used herein, refers to a virus that preferentially kills tumor cells as compared to normal cells. In addition, the term refers to viruses that can be engineered to carry a nucleic acid construct encoding a polypeptide, which is to be expressed in a tumor cell after infection of said tumor cell.

The term "nanoparticle," as used herein, refers to compositions that can carry a compound of interest, such as an antigenic polypeptide as described herein, and which can be functionalized on their surface with tumor-targeting or tumor-specific moieties. Examples of nanoparticles that can be engineered to actively target tumor cells are micelles and liposomes.

The term "dendritic cell," as used herein, refers to a professional antigen presenting cell (APC) that can take up an antigen such as an antigenic polypeptide into its cell, and presents the antigen, or an immunogenic part thereof together with an MHC class I complex or MHC class II complex. The term includes both immature dendritic cells ("imDC") and mature dendritic cells ("mDC"), depending on maturity. In certain embodiments, the dendritic cell is a mature dendritic cell. In certain embodiments, the dendritic cell is a mature dendritic cell obtained from a cell of cell line DCOne as deposited under the conditions of the Budapest treaty with the DSMZ under accession number DSMZ ACC3189 on 15 Nov. 2012. The process of obtaining mature dendritic cells from the deposited DCOne cell line is for instance described in EP2931878B1.

As used herein, the term "about" or "approximately" when referring to a measurable value, such as a distance from a tumor site, encompasses variations of ±20% or ±10%, ±5%, ±1%, or ±0.1% of a given value or range, as are appropriate to perform the methods disclosed herein.

Compositions and Formulations

As provided herein, a first aspect relates to a vaccination step comprising the administration of (vaccination with) a first composition (e.g., an immunogenic composition) comprising a non-tumor antigen (e.g., a non-human antigenic polypeptide as an immunogen), or comprising a nucleic acid encoding a non-tumor antigen (e.g., a nucleic acid encoding a non-human antigenic polypeptide). In certain embodiments, the first composition comprises a non-tumor antigen or a nucleic acid encoding a non-tumor antigen. In certain embodiments, the first composition optionally comprises one or more pharmaceutically-acceptable carriers, adjuvants, excipients and/or diluents.

As provided herein, a second aspect relates to a tumor-marking step comprising the administration of (vaccination with) a second composition (e.g., an immunogenic composition) comprising a non-tumor antigen (e.g., a non-human antigenic polypeptide as an immunogen), or comprising a nucleic acid encoding a non-tumor antigen (e.g., a nucleic acid encoding a non-human antigenic polypeptide). In certain embodiments, the second composition comprises a non-tumor antigen or a nucleic acid encoding the non-tumor antigen. In certain embodiments, the second composition optionally comprises one or more pharmaceutically-acceptable carriers, adjuvants, excipients and/or diluents.

In certain embodiments, the non-tumor antigen (e.g., non-human antigenic polypeptide) as disclosed herein serves two purposes. The first purpose is in generating an immune response. In certain embodiments, the immune response is a T-cell mediated immune response, against the antigen (e.g., non-human antigen, non-tumor antigen), by being incorporated in an immunogenic composition as an immunogen. The second purpose is in marking a tumor as a target for said immune response. The skilled person will directly understand that it is necessary that the tumor marking and mounting/generation of an immune response are matched in that the mounted immune response is directed against the tumor thus marked. "Matched" means that the immune response (to be) elicited is specifically directed against the antigenic polypeptide actively introduced into the tumor. In certain embodiments, the same or a corresponding antigenic epitope is used in marking the tumor and in elicitation of an immune response. Therefore, In certain embodiments, following the administration of a first composition (e.g., an immunogenic composition) as described herein to a subject, an immune response is elicited that is specifically directed against a tumor that is to be marked (or a tumor that is already marked) as a target for an immune response based on the same antigen.

In other words, the antigenic polypeptide in the second composition for marking, and the antigenic polypeptide in the first composition are matched, in that the immune response that is elicited following administration of the first composition to a subject is directed against a tumor marked with said antigenic polypeptide following intratumoral delivery of the same, or at least immunogenically the same, antigenic polypeptide. This may mean that the immune response elicited following administration of an immunogenic composition as described herein, is specifically directed to at least one T-cell epitope and/or B-cell epitope with which the tumor is to be marked (or is marked). In certain embodiments, the non-human antigenic polypeptide in said immunogenic composition is a polypeptide corresponding to the polypeptide used for tumor marking as described herein.

In certain embodiments, the immune response elicited following administration of a first composition (e.g., an immunogenic composition) as described herein, is a T-cell mediated immune response or a T-cell-dependent immune response. It is within the skilled person's capabilities to identify appropriate immunogens and/or adjuvants that activate the cellular arm of immunity. References that aid the skilled person in selecting appropriate antigens are for instance Bender et al., *J. Exp. Med,* 182:1663-1671 (1995); Bennett et al., *Nature,* 393:478-480 (1998); Kalinski and Moser, *Nature,* 5:251-260 (2005); Van Tenderloo et al., *PNAS,* 107:31, p. 13824-13829 (2010); Anguille et al., Blood, 12; 130(15):1713-1721 (2017); Tacken et al., Blood, 106:4, p. 1278-1285 (2005); Vigneron et al, Cancer Immunity, 13:15 (2013); and Cheever et al, Clin Cancer Res; 15:5323-5337 (2009), all of which are incorporated by reference herein in their entirety. The skilled person directly understands that antigenic polypeptides described in relation to immunogenic compositions stand also in relation to intratumoral delivery aspects, and vice versa. Examples of suitable antigens include proteins of viral, bacterial, fungal origin; allergens, toxins and venoms, or model antigens of various sources such as chicken egg ovalbumin and keyhole limpet hemocyanin from the giant keyhole limpet, *Megathura crenulata*. In certain embodiments, a suitable antigen is of bacterial origin. In certain embodiments, a suitable antigen is a diphtheria toxin. In certain embodiments, a suitable antigen is a non-toxic variant of diphtheria toxin. In certain embodiments, a suitable antigen is CRM197. Other suitable antigenic polypeptides are polypeptides employed in a prior vaccination of a subject, such as recall antigens, which are described in more detail herein below. Common vaccines, used in such vaccinations, may include different antigenic polypeptides, which can be multivalent in that they comprise different microbial (recall) antigens with or without adjuvants.

The term "recall antigen," as used herein, refers to an antigen (e.g., antigenic polypeptide) which has previously (e.g., prior to the occurrence of a tumor in the subject or prior to a tumor-marking step) been encountered by a subject. Recall antigens are those which have previously been encountered by the subject and for which there exists pre-existing memory lymphocytes in the subject. In certain embodiments, a recall antigen refers to an antigen (e.g., antigenic polypeptide) for which pre-existing memory lymphocytes exist in the subject, e.g., as a result of prior infections or vaccinations. In certain embodiments, a recall antigen refers to an antigenic polypeptide which has previously been encountered by a subject via vaccination. In certain embodiments, the recall antigen is an antigenic polypeptide for which there is pre-existing immunity in said subject.

The skilled person has multiple methods and means at his disposal that he can routinely apply in order to provide mounting of an immune response against a non-human antigenic polypeptide as an immunogen comprised in an immunogenic composition as described herein.

References that aid the skilled person in selecting adjuvants that direct the immune response towards cellular immunity are for instance Pashine et al., *Nature Medicine Supplement,* 11: S63-S68 (2005) and Awate et al., Frontiers in Immunology, 4:114, p. 1-10 (2013), the disclosures of which are incorporated by reference herein in their entirety. Examples of such adjuvants are aluminum mineral salts, oil-in-water emulsions, liposomes, toll-like receptor agonists or combinations thereof. Other adjuvants include liposomes, virosomes, MF59, Montanide, ISCOMs, QS-21, aluminum, ASO4, Poly I:C, MPL, GLA, imiquimod, CpG ODN, chitin, chitosan, β-glucan, or combinations thereof. (Temizoz et al. *Int Immunol.* 2016 July; 28(7): 329-338, the disclosure of which is incorporated by reference herein in its entirety).

In certain embodiments, compositions (e.g., a first composition comprising a non-tumor antigen and a second composition comprising the same non-tumor antigen) for use according to methods as described herein optionally comprise: a dendritic cell comprising the non-tumor antigen; a T-cell immune response-eliciting adjuvant; a T-cell immune response-eliciting virus or a virus-like particle comprising the non-tumor antigen or a nucleic acid encoding the non-tumor antigen; or a combination thereof.

In general, it is explicitly envisaged herein that embodiments that relate to the compositions for use in a method as described herein, also apply to aspects for instance the (i) non-tumor antigen (e.g., non-human antigenic polypeptide), or nucleic acid encoding the same for use in a method as described herein, (ii) immunogenic composition for use in a method as described herein, (iii) a method for eliciting an immune response, (iv) a method of treatment, and other aspects for use in a method as described herein where appropriate.

In certain embodiments, a method of the present disclosure employs the use of a first composition and a second composition. In certain embodiments, the first composition comprises an antigenic polypeptide (e.g., a non-tumor antigen) or a nucleic acid encoding an antigenic polypeptide. In certain embodiments, the first composition comprises an antigenic polypeptide. In certain embodiments, the first composition comprises a nucleic acid encoding an antigenic polypeptide. In certain embodiments, the first composition comprises a non-tumor antigen. In certain embodiments, the first composition comprises a nucleic acid encoding a non-tumor antigen.

In certain embodiments, the second composition comprises an antigenic polypeptide (e.g., a non-tumor antigen) or a nucleic acid encoding an antigenic polypeptide (i.e., the second composition comprises an antigenic polypeptide or a nucleic acid encoding the antigenic polypeptide which is the same as the antigenic polypeptide as in the first composition, or at least, immunologically the same antigenic polypeptide as in the first composition). In certain embodiments, the second composition comprises an antigenic polypeptide. In certain embodiments, the second composition comprises a nucleic acid encoding the antigenic polypeptide. In certain embodiments, the second composition comprises a non-tumor antigen. In certain embodiments, the second composition comprises a nucleic acid encoding a non-tumor antigen.

In certain embodiments, the first composition and/or the second composition may comprise a dendritic cell comprising an antigenic polypeptide (e.g., a non-tumor antigen) or a nucleic acid encoding an antigenic polypeptide. In certain embodiments, the first composition comprises a dendritic cell comprising an antigenic polypeptide or a nucleic acid encoding an antigenic polypeptide. In certain embodiments, the second composition comprises a dendritic cell comprising an antigenic polypeptide or a nucleic acid encoding an antigenic polypeptide. In certain embodiments, the first composition comprises a dendritic cell comprising a non-tumor antigen or a nucleic acid encoding a non-tumor antigen. In certain embodiments, the second composition comprises a dendritic cell comprising a non-tumor antigen or a nucleic acid encoding the non-tumor antigen.

In certain embodiments, the dendritic cell is employed as a dendritic cell vaccine, provided that such cells are loaded with the antigenic polypeptide as described herein. In certain embodiments, a composition (e.g., a first composition or a second composition) comprises a mature dendritic cell differentiated from a precursor cell line. In certain embodiments, a composition (e.g., a first composition or a second composition) comprises a mature dendritic cell that is CD34-positive, CD1a-positive, and CD83-positive. In certain embodiments, the dendritic cell is a cell of cell line DCOne as deposited at the DSMZ under accession number DSMZ ACC3189 on 15 Nov. 2012. See, e.g., WO 2014/006058, the disclosure of which is incorporated by reference herein in its entirety For example, in certain embodiments, the first composition and/or the second composition each comprise a dendritic cell of cell line DCOne comprising an antigenic polypeptide (e.g., a non-tumor antigen) or a nucleic acid encoding the antigenic polypeptide. Loading strategies for dendritic cells are discussed herein. The skilled person has ample guidance on how dendritic cells can be effectively used in the form of immunogenic compositions, which is for instance described in multiple references including EP2931878 B1, WO 2014/006058 A1, WO 2009/019320 and Saxena and Bhardwaj, Trends in Cancer, 4:2, p. 119-137 (2018), the disclosures of which are incorporated by reference herein in their entirety.

In certain embodiments, a pharmaceutically effective amount of a composition is administered. As used herein, an "effective amount" or a "pharmaceutically effective amount" of, e.g., a first composition or a second composition, refers to an amount effective, at dosages and for periods of time necessary to achieve an immune response. For example, an effective amount is sufficient to induce an immune response against an antigenic polypeptide (e.g., non-tumor antigen), optionally comprised in a dendritic cell. An effective amount is sufficient to induce an immune response against a tumor that has been marked using an antigenic polypeptide (e.g., non-tumor antigen) as described herein.

A first composition and/or a second composition as described herein may comprise any adjuvant known to those in the art. Adjuvants known in the art, regardless of the route of administration, may be employed to improve/enhance the immunogenicity of an antigenic polypeptide (e.g., a non-tumor antigen) comprised within a composition of the present disclosure. Adjuvants enhance the immunogenicity of an antigen (e.g., a composition comprising a non-tumor antigen) but are not necessarily immunogenic themselves.

Adjuvants have been used by those of skill in the art to improve immune responses to, e.g., vaccines. Adjuvants may be intrinsic or extrinsic. Intrinsic adjuvants may be derived from killed or attenuated bacteria used as vaccines. Extrinsic adjuvants maybe an immune modulating substance non-covalently linked to antigens and are formulated to enhance immune responses.

In certain embodiments, the first composition and/or the second composition may comprise a T-cell immune response-eliciting adjuvant. The term "T-cell immune response-eliciting," as used in relation to adjuvants or virus or virus-like particles herein, refers to enhancing CD4+ and/or CD8+ T-cell immune responses or driving the immune response towards CD4+ and/or CD8+ T-cell activation. The skilled person is well aware of adjuvants that can be employed for this purpose, such as liposomes, virosomes, MF59, Montanide, ISCOMs, QS-21, aluminum, ASO4, Poly I:C, MPL, GLA, imiquimod, CpG ODN, chitin, chitosan, β-glucan, or combinations thereof. (Temizoz et al. *Int Immunol.* 2016 July; 28(7): 329-338, the disclosure of which is incorporated by reference herein in its entirety).

In certain embodiments, adjuvants may be used specifically for parenteral modes of administration. Such adjuvants include, e.g., aluminum compounds (such as aluminum phosphate and aluminum hydroxide). The antigen can be precipitated with, or adsorbed onto, an aluminum compound according to standard protocols. Other adjuvants for parenteral modes of administration, as well as intratumoral or peri-tumoral modes of administration, are known to those of skill in the art.

A first composition and/or a second composition as described herein may comprise a virus, for example, a T-cell immune response-eliciting virus, or a virus-like particle (VLP), comprising an antigenic polypeptide (e.g., non-tumor antigen) or a nucleic acid encoding the antigenic polypeptide. It is within routine experimentation to design and produce a virus or VLP that can be employed in, or as a composition as described herein. Such viruses, especially T-cell immune response-eliciting viruses or VLPs, have been described extensively for vaccination purposes. This follows for instance from Frietze et al., *Curr Opin Virol.*, 18: 44-49 (2016); Koup and Douek, *Cold Spring Harb Perspect Med*, 2011; 1: a007252, the disclosures of which are incorporated by reference herein in their entireties. Examples of T-cell immune response-eliciting viruses or VLPs are for instance cowpox (vaccinia) viruses or derivatives thereof such as modified vaccinia virus Ankara (MVA), adenovirus or adeno-associated viruses and VLP's based on human papillomavirus, hepatitis B virus or VLP's engineered to present different tumor antigens. In certain embodiments, a composition as described herein (e.g., the second composition used in a tumor marking step) may comprise an oncolytic virus. Viruses that have been clinically tested to be oncolytic include, without limitation, adenovirus, reovirus, measles, herpes simplex, Newcastle disease virus, and vaccinia.

As used herein, the term "pharmaceutical composition" or "pharmaceutical formulation" refers to a preparation which is in such form as to permit the biological activity of an active ingredient contained therein to be effective (e.g., permit an antigenic polypeptide contained therein to be immunogenic), and which contains no additional unacceptably toxic components, with respect to toxicity when administered to a subject. A "pharmaceutically acceptable carrier" refers to an ingredient in a pharmaceutical formulation and/or composition, other than an active ingredient, which is nontoxic to a subject. Pharmaceutically acceptable carriers include, without limitation, a stabilizer, excipient, buffer, or preservative. In certain embodiments, the choice of carrier is determined in part by the particular method of administration. Accordingly, there are a variety of suitable formulations and compositions. Various formulations and compositions are known in the art that are suitable for, e.g., intratumoral administration, intramuscular administration, and other routes of administration.

In certain embodiments, the pharmaceutical composition can contain preservatives. Suitable preservatives may include, e.g., propylparaben, methylparaben, benzalkonium chloride, and sodium benzoate. In certain embodiments, a mixture of two or more preservatives is used. The preservative or mixtures thereof are typically present in an amount of about 0.0001% to about 2% by weight of the total composition.

Carriers are further described, e.g., by Remington's Pharmaceutical Sciences 16th edition, Osol, A. Ed. (1980). Pharmaceutically acceptable carriers are generally nontoxic to subjects administered compositions according to methods described herein at the dosages and concentrations employed, and include, but are not limited to: buffers such as citrate, phosphate, and other organic acids; antioxidants including methionine and ascorbic acid; low molecular weight (less than about 10 residues) polypeptides; hydrophilic polymers such as polyvinylpyrrolidone; proteins, such as gelatin, immunoglobulins, or serum albumin; preservatives (such as benzalkonium chloride; benzethonium chloride; phenol, butyl or benzyl alcohol; octadecyldimethylbenzyl ammonium chloride; alkyl parabens such as methyl or propyl paraben; catechol; resorcinol; hexamethonium chloride; 3-pentanol; cyclohexanol; and m-cresol); amino acids such as glutamine, asparagine, histidine, glycine, arginine, or lysine; monosaccharides, disaccharides, and other carbohydrates including dextrins, glucose, or mannose; sugars such as sucrose, trehalose, sorbitol, or mannitol; saltforming counter-ions such as sodium; metal complexes (e.g., Zn-protein complexes); non-ionic surfactants such as polyethylene glycol (PEG); and/or chelating agents such as EDTA.

In certain embodiments, buffering agents are included in the compositions. Suitable buffering agents include, for example, sodium citrate, citric acid, potassium phosphate, phosphoric acid, and various other acids and salts. In certain embodiments, a mixture of two or more buffering agents is used. The buffering agent or mixtures thereof are typically present in an amount of about 0.001% to about 4% by weight of the total composition. Methods for preparing administrable pharmaceutical compositions are known to those in the art. See, e.g., Remington: The Science and Practice of Pharmacy, Lippincott Williams & Wilkins; 21st ed. (May 1, 2005).

In certain embodiments, the compositions and formulations described herein can include aqueous solutions. The formulation or composition may also contain more than one active ingredient useful for the particular indication, disease, or condition (e.g., tumor type) being treated using a method as described herein. Such active ingredients are suitably present in combination in amounts that are effective for the purpose intended.

Formulations and compositions include those for oral, intravenous, intraperitoneal, subcutaneous, pulmonary, transdermal, intramuscular, intranasal, buccal, sublingual, or suppository administration. Formulations and compositions include those for any one of various routes of administration known in the art to those of skill in the art. In certain embodiments, the compositions are administered parenterally. The term "parenteral," as used herein, includes intravenous, intramuscular, subcutaneous, rectal, vaginal, and intraperitoneal administration.

In certain embodiments, compositions and formulations are provided as sterile liquid preparations, e.g., suspensions, emulsions, dispersions, viscous compositions, or isotonic aqueous solutions, which may in some embodiments be buffered to a selected pH. In certain embodiments, compositions and formulations are provided as gels, other viscous compositions, and solid compositions. Viscous compositions, can be formulated within the appropriate viscosity range to provide longer contact periods with specific tissues. Liquid or viscous compositions can comprise carriers, which can be a solvent or dispersing medium containing, e.g., saline, phosphate buffered saline, water, polyol (e.g., propylene glycol, liquid polyethylene glycol, glycerol) and suitable mixtures thereof.

Sterile injectable solutions can be prepared by incorporating into the compositions a solvent, such as in admixture with a suitable carrier, diluent, or excipient such as sterile water, physiological saline, glucose, dextrose, or the like. The compositions can contain gelling or viscosity enhancing additives, pH buffering agents, auxiliary substances such as wetting, dispersing, or emulsifying agents (e.g., methylcellulose), flavoring agents, colors, and/or preservatives, depending upon the route of administration and the preparation desired. Standard texts available to those having knowledge in the art may in some aspects be consulted to prepare suitable preparations.

Various additives which enhance the sterility and stability of the compositions, can be added, including without limitation chelating agents, antimicrobial preservatives, buffers, and antioxidants. Compositions can be kept sterile from or of the action of microorganisms by various antibacterial and antifungal agents, e.g., chlorobutanol, parabens, phenol, and sorbic acid. Prolonged absorption of the injectable pharmaceutical form can be brought about by the use of agents delaying absorption, for example, aluminum monostearate and gelatin.

The skilled person is aware of other suitable immunogenic compositions that mount an immune response against an antigen as described herein. For instance, other options involve the use of a subunit vaccine comprising an immunogen as described herein, and carrier proteins coupled to an immunogen.

Antigenic Polypeptides and Nucleic Acids

In certain embodiments, a composition for use in a method as described herein comprises an antigenic polypeptide (e.g., a non-tumor antigen), or a nucleic acid encoding the antigenic polypeptide. In certain embodiments, where the antigenic polypeptide is in a composition for intratumoral administration, the antigenic polypeptide is tumor-targeted or prepared for intratumoral delivery, or the nucleic acid encoding the antigenic polypeptide, is either tumor-targeted or is prepared for intratumoral administration. The skilled person will understand that the new concept of tumor antigen-independent vaccination can be realized with multiple methods and means known in the art, both with regard to the marking of a tumor, as well as with the vaccination that mounts an immune response against a marked tumor as already described.

In the medical methods described herein, marking or labelling of a tumor as a target for an immune response by employing a non-human antigenic polypeptide as described herein, occurs in vivo, not in vitro or ex vivo.

More specifically, the antigenic polypeptide or nucleic acid as described herein can be prepared for intratumoral delivery in a variety of ways, generally well known in the art. For instance, preparing may involve tumor-targeting of said polypeptide or nucleic acid, e.g., by preparing a tumor-targeting composition comprising said polypeptide or nucleic acid. A tumor-targeting composition comprises the polypeptide or nucleic acid in such a way that it is rendered tumor-specific. In certain embodiments, upon administration of a tumor-targeted polypeptide or nucleic acid to a subject, intratumoral delivery is effectuated on the basis of specificity for tumor tissue as compared to non-tumor tissue. Tumor specificity also indicates that it may allow for homing to a tumor so as to provide for intratumoral delivery.

In certain embodiments, the polypeptide prepared for intratumoral delivery, or the nucleic acid encoding said polypeptide, is tumor-targeted by using one or more of, e.g., a tumor-specific virus, including an oncolytic virus, comprising a nucleic acid encoding said polypeptide; a tumor-specific nanoparticle comprising said polypeptide or a nucleic acid encoding said polypeptide. In certain embodiments, said polypeptide or nucleic acid is tumor-targeted by using a tumor-targeting antibody, peptide, small molecule, or nucleic acid aptamer fused to said polypeptide or nucleic acid.

Another way of tumor-targeting a polypeptide or nucleic acid as described herein (so as to effectuate intratumoral delivery upon administration to a subject) involves the preparation of an oncolytic virus that comprises a nucleic acid encoding an antigenic polypeptide as described herein, which is engineered to express said nucleic acid into a tumor cell. That oncolytic viruses can be used to specifically target tumor cells is extensively described in the art, for instance in Lawler et al., *JAMA Oncol.* 1; 3(6):841-849 (2017); Howells et al., *Front Oncol.* 7:195 (2017), the disclosures of which are incorporated by reference herein in their entireties. In addition, as exemplified in for instance WO2014138314 A1 (the disclosure of which is incorporated by reference herein in its entirety), oncolytic viruses can be modified to engage tumor cells. It is also well-known in the art that oncolytic viruses can be used to deliver a nucleic acid construct encoding a polypeptide into a tumor cell, said virus being engineered to express said polypeptide into a tumor cell (Hutzler et al., *Scientific Reports*, 7: 16892 (2017); Grossardt et al., Human Gene Therapy, 24:644-654 (2013); Andtbacka et al., Journal of Clinical Oncology, 22:25, p. 2780-2788 (2015), the disclosures of which are incorporated by reference herein in their entireties). Subsequent intracellular processing of said polypeptide and antigen-presentation by said tumor cell provide for a tumor marked with an antigenic polypeptide as described herein. In other words, and in certain embodiments, following intratumoral delivery an antigenic polypeptide as described herein is presented by the MHC system of a tumor cell upon expression of said nucleic acid as described herein in a cell of said tumor to thereby mark said tumor as a target for an immune response.

Examples of oncolytic viruses that can be used for tumor-targeting are Adenovirus, Herpes simplex virus, Pox virus, Coxsackie virus, Maraba virus, Poliovirus, Measles virus, Newcastle Disease virus (Lal and Rajala, Cancer Gene Therapy, DOI 10.1038/s41417-018-0018-1 (2018); Haddad, Frontiers in Immunology, 7:96 (2017); Bommareddy et al., Nature Reviews Immunology (2018), the disclosures of which are incorporated by reference herein in their entireties).

A tumor-specific virus such as an oncolytic virus may be prepared in a pharmaceutical formulation adapted for parenteral administration. Such a formulation generally comprises a carrier such as for instance an aqueous or oily solution, dispersion, emulsion and/or suspension. Parenteral administration involves the injection or infusion into a body tissue or body fluid, whereby in certain embodiments, a syringe, needle, or catheter is used. In certain embodiments, the carrier is an aqueous solution, and in certain embodiments, distilled sterile water, saline, buffered saline, or another pharmaceutically acceptable excipient for injection. Examples of parenteral modes of administration are intravenous, intra-arterial, intra-peritoneal, subcutaneous, intra-muscular and intratumoral administration, which are well known to the person skilled in the art. In certain embodiments, a mode of administration of a tumor-specific virus such as an oncolytic virus is intravenous or intratumoral administration (Marelli et al., *Frontiers in Immunology*, 9:866 (2018), the disclosure of which is incorporated by reference herein in its entirety).

The dose to be administered of a tumor-specific virus such as an oncolytic virus is a pharmaceutically effective dose, i.e., a dose sufficient to deliver an antigenic polypeptide or nucleic acid as described herein into a tumor. It is routine practice to determine a dosing regimen for a tumor-specific virus.

An alternative way of tumor-targeting a polypeptide or nucleic acid as described herein (so as to effectuate intratumoral delivery upon administration to a subject), involves the preparation of a tumor-specific nanoparticle comprising an antigenic polypeptide or nucleic acid as described herein, the latter being engineered to express said nucleic acid in a tumor cell after delivery. In the field of cancer therapy, it is well known that a nanoparticle, which comprises a nanocarrier loaded or combined with for instance a polypeptide of interest, are extensively described in relation to specifically/selectively targeting (homing to) tumor cells and to subsequently deliver for instance a medicament such as a polypeptide to said tumor cell. Methods and means for tumor-targeting of nanoparticles or nanocarriers is generally known and is inter alia described in Olusanya et al., Molecules 23:907 (2018); Din et al., *Int J Nanomedicine*, 12:7291-7309 (2017); Alibakhshi et al., *J Control Release*, 268:323-334 (2017); and US 2013/0330399 A1, the disclosures of which are incorporated by reference herein in their entireties. In certain embodiments, tumor-specific delivery methods including, without limitation, use of nanoparticles, use of liposomes, and use of photochemical processes (e.g., photochemical internalization) may be used to enhance the delivery of an antigen (e.g., an antigenic polypeptide (e.g., a non-tumor antigen), or a nucleic acid encoding the antigenic polypeptide) into the cytosol of a tumor cell.

Photochemical internalization refers to a delivery method which involves the use of light and a photosensitizing agent for introducing otherwise membrane-impermeable molecules into the cytosol of a target cell, but which does not necessarily result in destruction or death of the target cell. In this method, the molecule to be internalized or transferred is applied to the cells in combination with a photosensitizing agent. Exposure of the cells to light of a suitable wavelength activates the photosensitizing agent which in turn leads to disruption of the intracellular compartment membranes and the subsequent release of the molecule into the cytosol. In photochemical internalization, the interaction between the photosensitizing agent and light is used to affect the cell such that intracellular uptake of the molecule is improved. Photochemical internalization as well as various photosensitizing agents are described in PCT Publication Nos. WO 96/07432, WO 00/54708, WO 01/18636, WO 02/44396, WO 02/44395, and WO 03/020309, U.S. Pat. Nos. 6,680, 301, 5,876,989, the disclosures of which are incorporated by reference herein in their entireties. In certain embodiments, photochemical internalization is used to deliver an antigen into the cytosol of a tumor cell. In certain embodiments, photochemical internalization is used to enhance the delivery of an antigen into the cytosol of a tumor cell.

The nanoparticle, or nanocarrier as main part of the nanoparticle, can be a polymeric nanoparticle, a micelle, a liposome, a nanogel or a carbon nanotube. Such a particle or carrier can be loaded with a compound of interest (such as a polypeptide) and actively targeted to a tumor by decorating such a particle or carrier with for instance antibodies or antibody fragments specific for a tumor antigen expressed on the surface of a tumor cell (see also the aforementioned references). Tumor-targeting moieties for a nanoparticle can in principle be any biological or chemical structure that displays affinity for a molecule expressed on a tumor cell, such as a peptide, oligopeptide or polypeptide, a protein, a hormone, a vitamin, an enzyme, a ligand of a tumor antigen or an antibody or antibody fragment that specifically binds to a tumor antigen. In certain embodiments, after administration of a tumor-targeted nanoparticle and subsequent homing and binding to a tumor cell, receptor-mediated endocytosis (internalization) allows for uptake of a nanocarrier by a tumor cell, thereby providing intracellular delivery of for instance a polypeptide of interest, which can be intracellularly processed and subsequently presented as an antigen in an MHC complex by a tumor cell.

Alternatively, after administration of a tumor-targeted nanoparticle and subsequent homing to a tumor and binding to a non-tumorous cell in the tumor, including an immune cell, such as a phagocytic cell or fibroblast, receptor-mediated endocytosis (internalization) allows for uptake of a nanocarrier by said cell, thereby providing intracellular delivery of for instance a polypeptide of interest in a tumor, which can be intracellularly processed and subsequently presented as an antigen in an MHC complex by said cell in said tumor. Specific examples of tumor-specific (or tumor-targeted) nanoparticles that can be employed for intratumoral delivery of an antigenic polypeptide or nucleic acid as described herein, are for instance poly(propylene) sulfide (PPS) nanoparticles, gold nanoparticles, PLGA nanoparticles, artificial exosomes, micelles or dendrimers.

In certain embodiments, a tumor-specific nanoparticle as described herein is prepared in a pharmaceutical formulation adapted for parenteral administration. Such a formulation generally comprises a carrier such as for instance an aqueous or oily solution, dispersion, emulsion and/or suspension. Parenteral administration involves the injection or infusion into a body tissue or body fluid, whereby in some cases, a syringe, needle, or catheter is used. In certain embodiments, the carrier is an aqueous solution, and in certain embodiments, the carrier is distilled sterile water, saline, buffered saline, or another pharmaceutically acceptable excipient for injection. Examples of parenteral modes of administration are intravenous, intra-arterial, intra-peritoneal, subcutaneous, intramuscular and intratumoral administration, which are well known to the person skilled in the art. In certain embodiments, a mode of administration of a tumor-specific nanoparticle is intravenous or intratumoral administration.

The dose of tumor-specific nanoparticle to be administered is a pharmaceutically effective dose, i.e., a dose sufficient to deliver an antigenic polypeptide or nucleic acid as described herein into a tumor. For a skilled person, it is routine practice to determine a dosing regimen for a tumor-specific nanoparticle.

In embodiments where the antigenic polypeptide or the nucleic acid as described herein is not tumor-targeted, they are prepared for intratumoral delivery by being in a form that allows for intratumoral injection. The skilled person directly understands that tumor-targeted compositions as described herein can also be administered intratumorally. The skilled person is aware of pharmaceutical formulations that are adapted for intratumoral injection, which may comprise a carrier such as for instance an aqueous or oily solution, dispersion, emulsion and/or suspensions. In embodiments where the antigenic polypeptide or nucleic acid as described herein are not tumor-targeted, the antigenic polypeptide and/or nucleic acid are, In certain embodiments, comprised in a dendritic cell, or the antigenic polypeptide is in an aqueous suspension or solution. In the same manner, in embodiments where the antigenic polypeptide or nucleic acid as described herein are not tumor-targeted, the antigenic polypeptide and/or nucleic acid can be comprised in a virus. It is thus explicitly envisaged herein that marking of a tumor with an antigenic polypeptide can occur at a tumor cell, but does not necessarily require intracellular processing and antigen presentation by a tumor cell itself. For instance, such intracellular processing can also be effectuated by other cell types in the tumor, including immune cells such as phagocytic cells—of which macrophages are an example—or fibroblasts. When dendritic cells are employed for tumor marking, marking of a tumor can be performed by antigen processing through the MHC system of the dendritic cell itself which dendritic cell is intratumorally injected. It is also known that dendritic cells, in particular allogeneic dendritic cells, may attract endogenous immune cells including NK cells and cross-prime dendritic cells which enforces the immune response in the tumor (Laurell et al. 2017, J for Immunother. Of Cancer 5: 52, the disclosures of which is incorporated by reference herein in its entirety).

Without being bound by theory, recruitment of previously 'untouched' immune cells into the tumor, or using pre-existing immunity that was, before tumor marking, not directed against a tumor, breaks immune tolerance resulting in further recruitment of immune cells directed against, i.e., tumor antigens of the tumor.

With regard to tumor marking, the skilled person is well aware of methods and means relating to loading of dendritic cells with an antigenic polypeptide or with a nucleic acid, such as mRNA, encoding such a polypeptide. See for instance Van Nuffel et al., *ISBT Science Series*, 8, 161-164 (2013); WO 2014/006058 A1; WO 2009/034172 A1, the disclosures of which are incorporated by reference herein in their entireties. In addition, the skilled person is well aware of methods and means for intratumoral injection of dendritic cells. See for instance US 2004/0057935 A1; Cripe et al., Molecular Therapy, 23: 3, p. 602-608 (2015); Hirooka et al., Oncotarget, 9:2, p. 2838-2847 (2018); Triozzi et al., Cancer, 89:12, p. 2646-2654 (2000); Laurell et al., *Journal for ImmunoTherapy of Cancer,* 5:52 (2017), the disclosures of which are incorporated by reference herein in their entireties. In certain embodiments, said polypeptide prepared for intratumoral delivery, or said nucleic acid encoding said polypeptide, is for intratumoral administration and is in the form of a dendritic cell. In certain embodiments, the dendritic cell is a (mature) dendritic cell obtained from a cell of cell line DCOne as described herein, comprising said polypeptide or said nucleic acid encoding said polypeptide as described herein. A person skilled in the art can routinely define a dosing regimen that suits intratumoral administration of a dendritic cell comprising an antigenic polypeptide or a nucleic acid encoding said polypeptide (such as an mRNA) as described herein. The same applies to an aqueous suspension or solution comprising an antigenic polypeptide as described herein.

It is clear that tumor marking can be effectuated via multiple different methods and means, as long as the tumor is marked with an antigenic polypeptide as described herein. For instance, tumor marking does not have to be effectuated exclusively by intracellular processing of antigenic polypeptides by tumor cells or other cell types in the tumor. It is also possible that the antigenic polypeptides prepared for intratumoral delivery are extracellular in the tumor and are thus not internalized by cells in said tumor. The presence of an extracellular antigenic polypeptide in the tumor will attract immune cells activated prior to marking by a vaccination step as described herein. In certain embodiments, such a vaccination step, and subsequent generation of immunity, is performed prior to tumor marking.

Further, the polypeptide, or nucleic acid encoding said polypeptide, prepared for intratumoral delivery are, in certain embodiments, accompanied by immuno-modulatory compounds, such as a chemokine and/or cytokine, that modulates the tumor, in certain embodiments, the tumor site or TME, to increase susceptibility to an immune response, in some cases to convert at least partially an immuno-tolerant tumor environment into an immuno-sensitive tumor environment or to facilitate (optimal) T-cell functionality in the tumor site or TME. Such an immunomodulatory compound is in some cases included in an tumor-specific virus, tumor-specific nano-particle, dendritic cell, or aqueous suspension or solution as described herein, either in the form of a polypeptide, or as a nucleic acid encoding such an polypeptide. In certain embodiments, examples of such immuno-modulatory compounds are e.g., GM-CSF, CCR5, XCL1, CCL20 and CCL21 (Mohan et al., Immunobiology, 223: 477-485 (2018); He et al., Journal of Experimental & Clinical Cancer Research, 29:37 (2010); Nguyen-Hoai et al., Cancer Gene Therapy, 19: 69-76 (2012), the disclosures of which are incorporated by reference herein in their entireties). Thus, for use in a method as described herein, said antigenic polypeptide, or a nucleic acid encoding said polypeptide, prepared for intratumoral delivery is in a composition that also comprises an immuno-modulatory compound (such as an immuno-modulatory polypeptide or a nucleic acid encoding said immuno-modulatory polypeptide), that converts at least partially an immuno-tolerant tumor site or TME into an immuno-sensitive tumor site or TME, and/or facilitates T-cell functionality in the tumor site or TME. In certain embodiments, said immuno-modulatory compound is an immunomodulatory polypeptide, or a nucleic acid encoding said immuno-modulatory polypeptide. In certain embodiments, the immuno-modulatory polypeptide is, or encodes for, GM-CSF, CCR5, XCL1 or CCL20, human GM-CSF, CCR5, XCL1 or CCL20. In certain embodiments, such an immuno-modulatory compound facilitates T-cell functionality in the tumor site or TME.

The term "immuno-tolerant TME," or "immuno-tolerant tumor site" as used herein, refers to a well-established phenomenon wherein the environment within a tumor provides for tolerance of, or insensitivity to, an antitumor immune response. In certain embodiments, a tumor site or TME is immuno-tolerant if it is more tolerant of, or more insensitive to, an immune response directed against a tumor in said TME, as compared to an immune response directed against a target in an environment outside said tumor, such as for instance an environment in or near healthy cells or healthy tissue.

The term "immuno-sensitive TME" or "immuno-sensitive tumor site," as used herein, refers to a situation wherein a tumor is sensitive or susceptible to an antitumor immune response.

With regard to the antigenic polypeptide for use in a method as described herein, it is an embodiment of the present disclosure that the polypeptide is not a tumor antigen. The term "tumor antigen," as used herein, includes both tumor associated antigens (TAAs) and tumor specific antigens (TSAs), including tumor neo-antigens. A tumor associated antigen is an antigen that is expressed on the surface of a tumor cell in higher amounts than is observed on normal cells or an antigen that is expressed on normal cells during fetal development. A tumor specific antigen is an antigen that is unique to tumor cells and is not expressed on normal cells. The term tumor antigen includes TAAs or TSAs that have been already identified and those that have yet to be identified.

Any antigenic polypeptide can be employed insofar it is immunogenic in a human subject. This includes both antigenic polypeptides of human and non-human origin. Therefore, an antigenic polypeptide can be a human or non-human antigenic polypeptide that is immunogenic in a human subject. In certain embodiments, the antigenic polypeptide is non-human. It is nonetheless explicitly envisaged herein that in aspects and/or embodiments that recite the term "non-human antigenic polypeptide," that aspect or embodiment can be amended so as to refer to "human antigenic polypeptide," or the term "human antigenic polypeptide" can be added in such aspects and/or embodiments. Human antigenic polypeptides that are immunogenic in a human subject are for instance embryonic, ovarian or testis polypeptides. This applies for instance to NY-ESO-1, WT-1 and the MAGE antigens (see for instance Cheever et al, Clin Cancer Res; 15:5323-5337 (2009); Vigneron et al, Cancer Immunity, 13:15 (2013) the disclosures of which are incorporated by reference herein in their entireties).

In one aspect, it is provided that the non-human antigenic polypeptides that are to be employed as the immunogen and marker in aspects of a method as described herein are not previously encountered by a subject as part of an immune response against a tumor. As such, in certain embodiments, the antigenic polypeptides are non-tumor antigens. In certain embodiments, the antigenic polypeptides are antigens that have not previously been encountered by the immune system of the subject and to which a subject is thus immunologically naïve, or are antigenic polypeptides previously encountered by a subject, but not as part of an immune response against a tumor, and in some cases for which protective immunity (memory T-cells and/or B-cells) exists. The latter can be highly beneficial, since it is not necessary to mount a de novo immune response, which takes time to mount, but instead taps into, or re-activates, existing immunity and directs it to a tumor according to the principle mechanism of a method as described herein. Therefore, in one embodiment, an non-human antigenic polypeptide as described herein is rarely if ever encountered (by the immune system) by a large portion of the human population intended for potential vaccination or is an antigenic polypeptide against which immunity pre-exists (is present in a subject), wherein said immunity is not directed against a tumor. The latter form of immunity can for instance be provided by a prior vaccination against an infectious disease earlier in life, including vaccination against hepatitis, such as hepatitis A and/or B, diphtheria, tetanus, pertussis, influenza, *Haemophilus influenzae* type b, polio (poliomyelitis), measles, mumps, rubella, varicella, human papillomavirus, *Streptococcus pneumoniae* (pneumonia), *Neisseria meningitides* (meningitis) or rotaviruses (rotaviral infection). Explicitly envisaged herein as non-human antigenic polypeptides for use according to a method as described herein are immunogenic polypeptides of one or more of hepatitis, including hepatitis A and/or B, diphtheria, tetanus, pertussis, influenza, *Haemophilus influenzae* type b, polio, measles, mumps, rubella, varicella, human papillomavirus, *Streptococcus pneumoniae, Neisseria meningitides* or rotaviruses. In certain embodiments, a non-human antigen polypeptide as described herein is a microbial polypeptide employed in a prior vaccination of said subject. In certain embodiments, the prior vaccination was against an infectious disease. In certain embodiments, the prior vaccination was against hepatitis A and/or B; diphtheria; tetanus; pertussis; influenza; *Haemophilus influenzae* type b; polio; measles; mumps; rubella; varicella; human papillomavirus, *Streptococcus pneumoniae, Neisseria meningitides* or rotaviruses. The skilled person understands that the polypeptide employed in a prior vaccination could be administered in different forms, such as part of (i) subunit vaccine, (ii) inactivated or attenuated micro-organism, (iii) toxoid vaccine (i.e., vaccine comprising inactivated toxins), etc.

In certain embodiments, a non-human antigenic polypeptide as described herein is a polypeptide selected from the group formed by VP3 from hepatitis A virus, including VP3 as identified in UniProtKB Acc. No. P08617, last modified: Aug. 1, 1988—v1; tetanus toxin from *Clostridium tetani*, including tetanus toxin as identified in UniProtKB Acc. No. P04958, last modified Jan. 23, 2007—v2; pertussis toxin from *Bordetella pertussis*, including pertussis toxin as identified in UniProtKB Acc. No. P04977, last modified: Aug. 13, 1987—v1; protein D from *Haemophilus influenzae*, including protein D as identified in UniprotKb Acc. No. R4R7Q5 (last modified: Jul. 24, 2013—v1); Vp1 capsid protein from poliovirus, including Vp1 capsid protein as identified in UniProtKB Acc. No. P03300, last modified: Jan. 23, 2007—v3; hemagglutinin from measles virus, including hemagglutinin as identified in UniProtKB Acc. No. P08362, last modified Aug. 1, 1988—v1; nucleoprotein from mumps virus, including nucleoprotein as identified in UniProtKB Acc. No. Q771S8, last modified: Jul. 5, 2004—v1; glycoprotein E1 or E2 from rubella virus, including glycoprotein E1 or E2 as identified in UniprotKb Acc. No. P08563, last modified: May 30, 2006—v2; immediate early 62 (IE62) protein from varicella zoster virus, including IE62 protein as identified in UniprotKb Acc. No. P09310, last modified: Jul. 1, 1989—v1; E6 or E7 protein from HPV16 or HPV18, including E6 or E7 protein as identified in UniprotKb Acc. Nos. P03126 (last modified: Jul. 21, 1986—v1), P03129 (last modified: Jul. 21, 1986—v1), P06463 (last modified: Jan. 1, 1988—v1) or P06788 (last modified: Apr. 1, 1990—v2); Spr96/2021, PV7 (7-valent) and/or PV13 (13-valent), in some cases, derived from or based on *Streptococcus pneumoniae; Neisseria* heparin binding antigen (NHBA), factor H binding protein (fHbp) or Neisserial adhesin A (nadA) from *Neisseria meningitides*, including NHBA as identified in UniprotKb Acc. No. Q7WYZ0 (last modified: Oct. 1, 2003—v1), fHbp as identified in UniprotKb Acc. No. B2CQ00 (last modified May 20, 2008—v1) or nadA as identified in UniprotKb Acc. No. Q9K105 (last modified Oct. 1, 2000—v1); VP8 or VP6 from rotaviruses, including VP8 as identified in UniprotKb Acc. No. P12473 (last modified: Mar. 24, 2009—v2) or VP6 as identified in UniprotKb Acc. No. P04509 (last modified: May 30, 2000—v2); and diphtheria toxin from *Corynebacterium diphtheria*, including a detoxified variant thereof referred to as CRM-197. It is noted that when reference is made to polypeptides employed in a prior vaccination, also included in said terminology are detoxified and immunogenic variants or parts of said polypeptides. In certain embodiments, an antigenic polypeptide as described herein is a recall antigen. In certain embodiments, an antigenic polypeptide as described herein is a microbial recall antigen.

In certain embodiments, the antigenic polypeptide chosen is matched with existing immunity (e.g., memory immunity in the form of memory T-cells and/or B-cells) in a subject, such that vaccination with such an antigenic polypeptide as immunogen, and tumor marking with such an antigenic polypeptide, taps into said pre-existing immunity (i.e., activates memory T-cells and/or B-cells to mount an immune response against said tumor). The skilled person can easily establish whether immunity against an antigenic polypeptide exists. In certain embodiments, the pre-existing immunity was generated prior to establishment of a tumor. In certain embodiments, the pre-existing immunity was generated early in life of the subject, e.g., at a time between the age of 0-20 years, at a time between the age of 1-12 or 1-6 years. In certain embodiments, the pre-existing immunity was generated at a time between the age of about 0-1 years, about 0-2 years, about 0-3 years, about 1-3 years, about 2-4 years, about 3-5 years, about 4-6 years, about 5-7 years, about 6-8 years, about 7-9 years, about 8-10 years, about 9-11 years, about 10-12 years, about 11-13 years, about 12-14 years, about 13-15 years, about 14-16 years, about 15-17 years, about 16-18 years, about 17-19 years, about 18-20 years, at a time before the age of 1, at a time before the age of 2, at a time before the age of 3, at a time before the age of 4, at a time before the age of 5, at a time before the age of 6, at a time before the age of 7, at a time before the age of 8, at a time before the age of 9, at a time before the age of 10, at a time before the age of 11, at a time before the age of 12, at a time before the age of 13, at a time before the age of 14, at a time before the age of 15, at a time before the age of 16, at a time before the age of 17, at a time before the age of 18, at a time before the age of 19, at a time before the age of 20, at a time before the age of 25, at a time before the age of 30, at a time before the age of 35, at a time before the age of 40, at a time before the age of 45, at a time before the age of 50, at a time before the age of 60, at a time before the age of 70, at a time before the age of 80, at a time before the age of 90, at a time before the age of 100, or at a time during the life of the subject.

In order to capitalize on pre-existing immunity, in certain embodiments, dormant immune cells are reactivated by at least one immunization with an immunogenic composition as described herein.

In certain embodiments, the antigenic polypeptide used in aspects of a method as described herein is not previously encountered by a subject as part of an immune response against a tumor, is (i) not (or rarely) encountered by a human subject as part of an immune response, or (ii) is encountered as part of an immune response, but not an immune response against a tumor, and wherein protective immunity is present in a subject.

In certain embodiments, the antigenic polypeptide as described herein mounts an immune response in cancer patients, e.g., patients suffering from a tumor. In certain embodiments, the antigenic polypeptide mounts an immune response in at least 90% of the patients intended for potential vaccination using a method as described herein. For example, the antigenic polypeptide mounts an immune response in at least 91%, 92%, 93%, 94%, 95%, 96%, 97%, 98%, 99%, or 100% of the patients intended for potential vaccination using a method as described herein. The immune response thus mounted in cancer patients can be a de novo response due to the fact that the patients' immune system has not previously encountered this immunogen.

In certain exemplary embodiments, the antigenic polypeptide is a non-mammalian polypeptide, such as a microbial polypeptide, or a synthetic polypeptide. In certain exemplary embodiments, the antigenic polypeptide is selected from the group formed by keyhole limpet hemocyanin (KLH), green fluorescent protein (GFP) including enhanced green fluorescent protein (eGFP), luciferase, beta-galactosidase and a diphtheria toxin.

The term "microbial polypeptide," as used herein, refers to a polypeptide of a micro-organism, which includes bacteria, archaea, protists, fungi, unicellular plants and viruses.

In certain embodiments, the antigenic polypeptide (e.g., non-human antigenic polypeptide) is a bacterial polypeptide, a polypeptide originating from an organism of the Archaea domain, a fungal polypeptide or a viral polypeptide. In certain embodiments, the antigenic polypeptide is a plant polypeptide. Also envisaged are a non-human mammalian polypeptide such as a polypeptide of a non-human primate, a rodent (e.g., mice and rats), a rabbit, a pig, a sheep, a goat, a cow, a horse and a donkey, a birds (e.g., a chicken, a turkey, a duck, a goose and the like). The antigenic polypeptide can also be a polypeptide of a snail or other mollusk, e.g., one of the genus of Megathura, or Megathura crenulata.

In certain embodiments, antigenic polypeptides that are not mammalian polypeptides find certain use in a method as described herein, since non-mammalian antigenic polypeptides are more immunogenic than mammalian polypeptides when administered to a human subject. Examples of suitable non-mammalian antigenic polypeptides are for instance green fluorescent protein (GFP) including enhanced green fluorescent protein (eGFP), luciferase and beta-galactosidase.

One example of an antigenic polypeptide is Keyhole Limpet Hemocyanin (KLH) of Megathura crenulata. KLH can be either KLH1 (amino acid sequence is provided in UniProtKB-Q53IP9, last modified: Feb. 19, 2014—v2) or KLH2 (amino acid sequence is provided in UniProtKB-Q1MVA1, last modified: May 30, 2006—v1). KLH is an example of a highly immunogenic antigen, which has been widely used as a universal immunogen and vaccine carrier.

Another example of an antigenic polypeptide is a diphtheria toxin, which term includes detoxified variants thereof such as cross-reacting material (CRM)-197. In certain embodiments, the antigenic polypeptide (e.g., non-tumor antigen) is CRM197. In certain embodiments, diphtheria toxin has the amino acid sequence as indicated in SEQ ID NO:1. In certain embodiments, a detoxified variant of diphtheria toxin is CRM-197, which has the amino acid sequence as indicated in SEQ ID NO:1, except for glycine (G) at amino acid residue position 52 being substituted with glutamic acid (E). The term also includes variants of diphtheria toxin that have at least 90%, at least 95%, at least 96%, at least 97%, at least 98%, or at least 99% sequence identity to SEQ ID NO:1 or to a part of SEQ ID NO:1 having a continuous stretch of least 100, at least 200 or at least 300 amino acid residues. In certain embodiments, the continuous stretch is in—or is—the amino acid region indicated by positions 1-385 of SEQ ID NO:1. Alternatively, such variants include proteins having the amino acid sequence of SEQ ID NO:1, except that 1-50, 1-20, or 1-10, amino acid residues are deleted, inserted or substituted. Such variants may exhibit antigenicity and/or immunogenicity as described herein.

The term "% sequence identity" is defined herein as the percentage of amino acids in an amino acid sequence that is identical with the amino acids in an amino acid sequence of interest, after aligning the sequences and optionally introducing gaps, if necessary, to achieve the maximum percent sequence identity. Methods and computer programs for alignments are well known in the art. Sequence identity is calculated over substantially the whole length, in some cases, the whole (full) length, of an amino acid sequence of interest. The skilled person understands that consecutive amino acid residues in one amino acid sequence are compared to consecutive amino acid residues in another amino acid sequence.

In certain embodiments, in methods as described herein wherein diphtheria toxin is employed for intratumoral delivery of an antigenic polypeptide, the tumor is a tumor that expresses the HB-EGF receptor. In certain embodiments, a tumor that expresses the HB-EGF receptor is selected from the group consisting of an ovarian tumor; a lung tumor; a bladder tumor; a gastric tumor; a pancreatic tumor; a breast tumor; a liver tumor (e.g., hepatocellular carcinoma); a brain tumor (e.g., glioblastoma, astrocytoma, brain stem glioma, mixed glioma, oligodendroglioma, optic nerve glioma, and other tumors that originate in the brain, e.g., anaplastic astrocytoma, fibrillary astrocytoma, pilocytic astrocytoma); a neuroblastoma; a lymphoma including Hodgkin lymphoma or non-Hodgkin lymphoma, a histiocytic lymphoma or anaplastic large cell lymphoma; and a leukemia (e.g., AML, CML or ALL). In certain embodiments, the tumor that expresses the HB-EGF receptor is a malignant tumor selected from the group formed by ovarian cancer; lung cancer; bladder cancer; gastric cancer; pancreatic cancer; breast cancer; hepatocellular carcinoma; brain cancer (e.g., glioblastoma); neuroblastoma; lymphoma including Hodgkin lymphoma or non-Hodgkin lymphoma, histiocytic lymphoma or anaplastic large cell lymphoma; and leukemia, e.g., AML, CML or ALL.

Also provided herein are nucleic acids encoding the antigenic polypeptide as described herein. In certain embodiments, a nucleic acid encoding CRM197 for use in a method as described herein, is provided.

Amino acid sequences of proteins or polypeptides as described herein can be produced by methods and means generally available in the art. For instance, the person skilled in the art will understand how to generate a DNA sequence that encodes a fusion protein as described herein and how to manufacture and isolate a nucleic acid molecule with said DNA sequence using generally known recombinant DNA techniques. In certain embodiments, the sequence of the nucleic acid molecule is codon-optimized for expression in a host cell. In this way codons are used that are favored for high level expression in a specific host cell. In certain embodiments, nucleic acid molecules are inserted in an expression vector using recombinant DNA techniques known by the person skilled in the art. Expression vectors direct the expression of a fusion protein as described herein in a host cell. In certain embodiments, these expression vectors are replicable in a host cell, either as episomes or as part of the chromosomal DNA. Further, in certain embodiments, the expression vector comprises (i) a strong promoter/enhancer, such as the CMV or SV40 promoter, (ii) an optimal translation initiation sequence, such as a ribosomal binding site and start codon, and/or a KOZAK consensus sequence and (iii) a transcription termination sequence, including a poly(A) signal when the protein is expressed in eukaryotic cells. Suitable expression vectors include plasmids and viral vectors such as adenoviruses, adeno-associated viruses and retroviruses. The person skilled in the art will understand that the expression vector to be used is dependent on the host cell that is used for expression of a recombinant protein. In certain embodiments, an expression vector is suited for expression of a nucleic acid in a prokaryotic cell including a bacterial cell, or in a eukaryotic host cell, such as a yeast cell and a mammalian cell. A suitable example is mammalian expression vector pCMV4.

As an alternative, a nucleic acid molecule may be inserted in the genome of a host cell. In certain embodiments, the insertion is at a locus or within a region that ensures expression of a nucleic acid molecule as described herein in the host cell.

Suitable host cells include prokaryotic and eukaryotic cells, such as bacterial cells, yeast cells, insect cells, animal cells, mammalian cells, murine cells, rat cells, sheep cells, simian cells and human cells. Examples of suitable eukaryotic host cells include, but are not limited to HEK 293 cells, the hamster cell line CHO and BHK-21; the murine host cells NIH3T3, NSO and C127; the simian host cells COS and Vero; and the human host cells HeLa, PER.C6, U-937 and Hep G2. Suitable cells are available from public sources such as ATCC and Life Technologies. A number of transfection techniques are known in the art, see, e.g., Graham et al., 1973. Virology 52: 456; Green et al., 2012. "Molecular Cloning: A Laboratory Manual," CSHL Press; Davis et al., "Basic Methods in Molecular Biology," 1986, Elsevier; and Chu et al., 1981. Gene 13: 197, the disclosures of which are incorporated by reference herein in their entireties. The person skilled in the art may employ techniques as described in these references to introduce one or more exogenous nucleic acid molecules into suitable host cells. An example of a host cell for the production of a fusion protein as described herein is a HEK 293 cell.

The antigenic polypeptide as described herein can also be a synthetic polypeptide, e.g., a synthetic polypeptide that is designed for eliciting a strong cellular immune response upon administration to a human subject.

When the antigenic polypeptide is for administration as an immunogen, it may comprise a further polypeptide or conjugation partner so as to enhance elicitation of an immune response. Thus, said immunogen can be a fusion polypeptide comprising said antigenic polypeptide and for instance a carrier protein.

Methods of Administration

Provided herein are methods for treating a tumor (e.g., a solid tumor) in a subject. Also provided are methods for generating an immune response against a tumor in a subject. Such methods comprise a vaccination step comprising distally administering a first composition, and a tumor-marking step comprising intratumorally or peri-tumorally administering a second composition. Such methods comprise a vaccination step comprising administering a first composition to the subject at a site distal to a tumor site, wherein the first composition comprises a non-tumor antigen or a nucleic acid encoding the non-tumor antigen; and a tumor-marking step comprising administering a second composition to the subject at the tumor site, wherein the second composition comprises the non-tumor antigen or a nucleic acid encoding the non-tumor antigen. The first composition and the second composition are described elsewhere herein.

In certain embodiments, the vaccination step comprises administering the first composition to a site that is away from the tumor. In certain embodiments, the vaccination step comprises administering the first composition to a site distal to the tumor. In certain embodiments, distal administration of an immunogenic composition (e.g., a first composition) in a vaccination step as described herein is through the parenteral route, which includes intravenous, intra-arterial, subcutaneous, intradermal, intranodal, intralymphatic and intramuscular administration, which are all well known to the person skilled in the art. In certain embodiments, distal administration of an immunogenic composition (e.g., a first composition) described herein is delivered by a mode selected from the group consisting of intramuscular injection, subcutaneous injection, intravenous injection, intraarterial injection, intraperitoneal injection, intrasternal injection, intradermal injection, transcutaneous injection, transdermal injection, and delivery to the interstitial space of a tissue In certain embodiments, the vaccination step comprises administration of the first composition, wherein the administration is not intratumoral, but instead is extratumoral and is in some cases intramuscular, intradermal, intravenous, intranodal or intralymphatic, intradermal, intravenous or a combination thereof. In certain embodiments, the vaccination step comprising administering the first composition intramuscularly at a site distal to the tumor site.

In certain embodiments, the vaccination step comprises distally administering the first composition at a site at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, at least about 45 mm, at least about 50 mm, at least about 60 mm, at least about 70 mm, at least about 80 mm, at least about 90 mm, at least about 10 cm, at least about 20 cm, at least about 30 cm, at least about 40 cm, at least about 50 cm, 50 cm or more away from the tumor (e.g., the edge of the tumor, or the center of the tumor). In certain embodiments, the vaccination step comprises administering a first composition to the subject at a site distal to a tumor site, therein the site distal to the tumor site is at least about 0.1 mm, at least about 0.2 mm, at least about 0.3 mm, at least about 0.4 mm, at least about 0.5 mm, at least about 0.6 mm, at least about 0.7 mm, at least about 0.8 mm, at least about 0.9 mm, at least about 1 mm, at least about 2 mm, at least about 3 mm, at least about 4 mm, at least about 5 mm, at least about 6 mm, at least about 7 mm, at least about 8 mm, at least about 9 mm, at least about 10 mm, at least about 15 mm, at least about 20 mm, at least about 25 mm, at least about 30 mm, at least about 35 mm, at least about 40 mm, at least about 45 mm, at least about 50 mm, at least about 60 mm, at least about 70 mm, at least about 80 mm, at least about 90 mm, at least about 10 cm, at least about 20 cm, at least about 30 cm, at least about 40 cm, at least about 50 cm, 50 cm or more away from the tumor (e.g., the edge of the tumor, or the center of the tumor).

In certain embodiments, the vaccination step comprises distally administering the first composition at a site in an organ system that is different to the organ system in which the tumor resides. In certain embodiments, the vaccination step comprises administering a first composition into an organ system that is different than the organ system in which the tumor resides. For example, if the tumor resides at or in an ovary (e.g., an epithelial ovarian cancer), the vaccination step comprises distally administering the first composition at a site in an organ system that is not the ovary, e.g., the liver, kidney, etc. The term "organ" or "organ system" as used herein refers to a group of tissues with similar functions. Examples of organ systems include, without limitation, the muscular system, the digestive system (e.g., stomach, small intestine, large intestine, liver, pancreas, etc.), the respiratory system (e.g., lungs), the urinary system (e.g., kidneys, bladder, etc.), the reproductive organs (e.g., male and female reproductive system, ovaries, placenta, prostate, etc.), the endocrine system, the circulatory system, the nervous system (e.g., central and peripheral nervous systems), and the integumentary system (e.g., skin, subcutaneous tissue).

In certain embodiments, the vaccination step comprises distally administering the first composition at a site contralateral to the tumor site. In certain embodiments, the vaccination comprises administering a first composition at a site contralateral to the tumor (a site in which the tumor resides). For example, if the tumor resides at or in an ovary, the vaccination step comprises distally administering the first composition at or in the contralateral ovary. For example, if the tumor resides at or in the left ovary, the vaccination step comprises distally administering the first composition to the right ovary. For example, if the tumor resides at or in an ovary, the vaccination step comprises administering a first composition at or in the contralateral ovary. For example, if the tumor resides at or in the left ovary, the vaccination step comprises administering a first composition to the right ovary.

In certain embodiments, a method as described herein comprises one or more vaccination steps. In certain embodiments, a second, a third, a fourth, a fifth, a sixth, a seventh, or more vaccination steps are performed. The skilled artisan will recognize that any, if any, subsequent vaccination steps are performed, the subsequent vaccination steps are envisioned to incorporate any of the embodiments of a vaccination step described herein.

In certain embodiments, the tumor-marking step comprises intratumorally or peri-tumorally administering the second composition. In certain embodiments, the tumor-marking step comprises administering a second composition to the subject at the tumor site. In certain embodiments, the tumor-marking step comprises administering a second composition into the tumor or proximal to the tumor. Accordingly, use of an antigenic polypeptide described herein prepared for intratumoral delivery as described herein, is provided.

Also provided is a method for eliciting an immune response against a subject suffering from a tumor, comprising the steps of administering to a subject suffering from a tumor a pharmaceutically effective amount of an antigenic polypeptide, or a nucleic acid encoding said polypeptide, prepared for intratumoral delivery; and administering to said subject a pharmaceutically effective amount of an immunogenic composition comprising said polypeptide as an immunogen, or comprising a nucleic acid encoding said immunogen, and optionally one or more pharmaceutically-acceptable carriers, adjuvants, excipients and/or diluents. In certain embodiments, the (i) polypeptide/nucleic acid prepared for intratumoral delivery, (ii) the immunogenic composition, and (iii) the medical use as described herein.

Such a method may further comprise the step of allowing an MHC peptide antigen complex to be produced from said polypeptide following intratumoral delivery of said polypeptide, or said nucleic acid encoding said polypeptide, prepared for intratumoral delivery.

In certain embodiments, administration of the first composition and the second composition according to a method as described herein, elicits a T cell mediated immune response against the antigenic polypeptide or the MHC peptide antigen complex.

Also provided herein is a method for treating a tumor in a subject in need, comprising: (1) a vaccination step comprising distally administering a first composition comprising an antigenic polypeptide or a nucleic acid encoding the antigenic polypeptide, wherein the administration is performed distal to the tumor site; and (2) a tumor-marking step comprising intratumorally or peri-tumorally administering a second composition comprising an antigenic polypeptide or a nucleic acid encoding the antigenic polypeptide. Accordingly, in certain embodiments, provided herein is a method for treating a tumor in a subject in need, comprising: (1) a vaccination step comprising distally administering a first composition comprising a non-tumor antigen or a nucleic acid encoding the non-tumor antigen, wherein the administration is performed distal to the tumor site; and (2) a tumor-marking step comprising intratumorally or peri-tumorally administering a second composition comprising the non-tumor antigen or a nucleic acid encoding the non-tumor antigen. Also provided herein is a method for treating a tumor in a subject in need, comprising: (1) a vaccination step comprising administering a first composition to the subject at a site distal to a tumor site, wherein the first composition comprises a non-tumor antigen or a nucleic acid encoding the non-tumor antigen; and (2) a tumor-marking step comprising administering a second composition to the subject at the tumor site, wherein the second composition comprises the non-tumor antigen or a nucleic acid encoding the non-tumor antigen. Accordingly, in certain embodiments, provided herein is a method for treating a tumor in a subject in need, comprising: (1) a vaccination step comprising administering a first composition to the subject at a site distal to a tumor site, wherein the first composition comprises a non-tumor antigen or a nucleic acid encoding the non-tumor antigen; and (2) a tumor-marking step comprising administering a second composition to the subject at the tumor site, wherein the second composition comprises the non-tumor antigen or a nucleic acid encoding the non-tumor antigen.

Also provided herein is a method for generating an immune response against a tumor in a subject in need, comprising: (1) a vaccination step comprising distally administering a first composition comprising an antigenic polypeptide or a nucleic acid encoding the antigenic polypeptide, wherein the administration is performed distal to the tumor site; and (2) a tumor-marking step comprising intratumorally or peri-tumorally administering a second composition comprising an antigenic polypeptide or a nucleic acid encoding the antigenic polypeptide. Accordingly, in certain embodiments, provided herein is a method for generating an immune response against a tumor in a subject in need, comprising: (1) a vaccination step comprising distally administering a first composition comprising a non-tumor antigen or a nucleic acid encoding the non-tumor antigen, wherein the administration is performed distal to the tumor site; and (2) a tumor-marking step comprising intratumorally or peri-tumorally administering a second composition comprising the non-tumor antigen or a nucleic acid encoding the non-tumor antigen. Also provided herein is a method for generating an immune response against a tumor in a subject in need, comprising: (1) a vaccination step comprising administering a first composition to the subject at a site distal to a tumor site, wherein the first composition comprises a non-tumor antigen or a nucleic acid encoding the non-tumor antigen; and (2) a tumor-marking step comprising administering a second composition to the subject at the tumor site, wherein the second composition comprises the non-tumor antigen or a nucleic acid encoding the non-tumor antigen. Accordingly, in certain embodiments, provided herein is a method for generating an immune response against a tumor in a subject in need, comprising: (1) a vaccination step comprising administering a first composition to the subject at a site distal to a tumor site, wherein the first composition comprises a non-tumor antigen or a nucleic acid encoding the non-tumor antigen; and (2) a tumor-marking step comprising administering a second composition to the subject at the tumor site, wherein the second composition comprises the non-tumor antigen or a nucleic acid encoding the non-tumor antigen.

Also provided is a method for eliciting or directing an immune response against a tumor in a subject in need, comprising: (1) a vaccination step comprising distally administering a first composition comprising an antigenic polypeptide or a nucleic acid encoding the antigenic polypeptide, wherein the administration is performed distal to the tumor site; and (2) a tumor-marking step comprising intratumorally or peri-tumorally administering a second composition comprising an antigenic polypeptide or a nucleic acid encoding the antigenic polypeptide. Accordingly, in certain embodiments, provided herein is a method for eliciting or directing an immune response against a tumor in a subject in need, comprising: (1) a vaccination step comprising distally administering a first composition comprising a non-tumor antigen or a nucleic acid encoding the non-tumor antigen, wherein the administration is performed distal to the tumor site; and (2) a tumor-marking step comprising intratumorally or peri-tumorally administering a second composition comprising the non-tumor antigen or a nucleic acid encoding the non-tumor antigen. Also provided is a method for eliciting or directing an immune response against a tumor in a subject in need, comprising: (1) a vaccination step comprising administering a first composition to the subject at a site distal to a tumor site, wherein the first composition comprises a non-tumor antigen or a nucleic acid encoding the non-tumor antigen; and (2) a tumor-marking step comprising administering a second composition to the subject at the tumor site, wherein the second composition comprises the non-tumor antigen or a nucleic acid encoding the non-tumor antigen. Accordingly, in certain embodiments, provided herein is a method for eliciting or directing an immune response against a tumor in a subject in need, comprising: (1) a vaccination step comprising administering a first composition to the subject at a site distal to a tumor site, wherein the first composition comprises a non-tumor antigen or a nucleic acid encoding the non-tumor antigen; and (2) a tumor-marking step comprising administering a second composition to the subject at the tumor site, wherein the second composition comprises the non-tumor antigen or a nucleic acid encoding the non-tumor antigen.

In certain embodiments, the antigenic polypeptide of a method as described herein is CRM197. Accordingly, also provided herein is a method for treating a tumor in a subject in need, comprising: (1) a vaccination step comprising administering a first composition to the subject at a site distal to a tumor site, wherein the first composition comprises CRM197 or a nucleic acid encoding CRM197; and (2) a tumor-marking step comprising administering a second composition to the subject at the tumor site, wherein the second composition comprises CRM197 or a nucleic acid encoding CRM197. Also provided herein is a method for generating an immune response against a tumor in a subject in need, comprising: (1) a vaccination step comprising administering a first composition to the subject at a site distal to a tumor site, wherein the first composition comprises CRM197 or a nucleic acid encoding CRM197; and (2) a tumor-marking step comprising administering a second composition to the subject at the tumor site, wherein the second composition comprises CRM197 or a nucleic acid encoding CRM197. Also provided is a method for eliciting or directing an immune response against a tumor in a subject in need, comprising: (1) a vaccination step comprising administering a first composition to the subject at a site distal to a tumor site, wherein the first composition comprises CRM197 or a nucleic acid encoding CRM197; and (2) a tumor-marking step comprising administering a second composition to the subject at the tumor site, wherein the second composition comprises CRM197 or a nucleic acid encoding CRM197.

In certain embodiments, the vaccination step and the tumor-marking step are temporally separated. Accordingly, in certain embodiments, the vaccination step is performed prior to the tumor-marking step. In certain embodiments, the tumor-marking step is performed subsequent to the vaccination step. In certain embodiments, a certain time has elapsed after the vaccination step before the tumor-marking step is performed. In certain embodiments, the amount of time elapsed after the vaccination step is sufficient for the subject to mount an immune response to the antigenic polypeptide comprised within the administered first composition. In certain embodiments, the time between the vaccination step and the tumor-marking step is sufficient for an immune response to be mounted as a result of the vaccination step.

For example, a primary immune response can be mounted as a result of the vaccination step. In the case of a primary immune response, it may take about 7 days to about 21 days to mount the primary immune response. In another example, a secondary immune response can be mounted as a result of the vaccination step, e.g., in response to an antigenic polypeptide for which the subject has pre-existing immunity against. In the case of a secondary immune response, it may take about 2 days to about 3 days to mount the secondary immune response. Accordingly, in certain embodiments, the time between the vaccination step and the tumor-marking step is from about 1 day to about 21 days, from about 1 day to about 22 days, from about 1 day to about 23 days, from about 1 day to about 24 days, from about 1 day to about 3 weeks, from about 1 day to about 4 weeks, from about 1 day to about 5 weeks, from about 1 day to about 10 weeks, from about 1 day to about 15 weeks, from about 1 day to about 20 weeks, from about 1 day to about 25 weeks, from about 1 day to about 30 weeks, from about 1 day to about 35 weeks, from about 1 day to about 40 weeks, from about 1 day to about 45 weeks, from about 1 day to about 50 weeks, from about 1 day to about 1 year, from about 1 day to about 2 years, from about 1 day to about 3 years, from about 1 day to about 4 years, from about 1 day to about 5 years, from about 1 day to about 10 years, from about 1 day to about 15 years, from about 1 day to about 20 years, from about 1 day to about 25 years, from about 1 day to about 30 years, from about 1 day to more than about 30 years, and any intervening amount of time thereof. In certain embodiments, the time between a vaccination step and the tumor-marking step is about 1 day to about 1 month, 14 days to about 2 months, 1 month to about 3 months, 2 months to about 5 months, 4 months to about 6 months, 5 months to about 7 months, 6 months to about 8 months, 7 months to about 9 months, 8 months to about 10 months, 9 months to about 11 months, 10 months to about 12 months, 11 months to about 13 months, 12 months to about 14 months, 13 months to about 15 months, 14 months to about 16 months, 15 months to about 17 months, 16 months to about 18 months, 17 months to about 19 months, 18 months to about 20 months, 19 months to about 21 months, 20 months to about 22 months, 21 months to about 23 months, 22 months to about 24 months, 3 months to about 1 year, 6 months to about 1 year, 1 year to about 2 years, 1.5 years to about 3 years, 2 years to about 3.5 years, 2.5 years to about 4 years, 3 years to about 4.5 years, 3.5 years to about 5 years, 4 years to about 5.5 years, 4.5 years to about 6 years, 5 years to about 6.5 years, 5.5 years to about 7 years, 6 years to about 7.5 years, 6.5 years to about 8 years, 7 years to about 8.5 years, 7.5 years to about 9 years, 8 years to about 9.5 years, 8.5 years to about 10 years, and any intervening range of time thereof.

In certain embodiments, the time between the vaccination step and the tumor-marking step is about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 4 weeks, about 5 weeks, about 6 weeks, about 7 weeks, about 8 weeks, about 9 weeks, about 10 weeks, about 20 weeks, about 30 weeks, about 40 weeks about 50 weeks, about 1 year, about 2 years, about 3 years, about 4 years, about 5 years, about 10 years, about 15 years, about 20 years, about 25 years, about 30 years, or more, and any intervening amount of time thereof. In certain embodiments, the time between the vaccination step and the tumor-marking step is about 2 days to about 21 days. In certain embodiments, the time between the vaccination step and the tumor-marking step is about 2 days to about 3 days. In certain embodiments, the time between the vaccination step and the tumor-marking step is about 7 days to about 21 days.

The contents of the documents referred to throughout the present disclosure are each incorporated herein by reference in their entirety.

For the purpose of clarity and a concise description, features are described herein as part of the same or separate aspects and embodiments thereof. For instance, embodiments relating to polypeptides may also apply to nucleic acids encoding such polypeptides, and vice versa. The same applies for instance to embodiments that relate to medical uses defined in product for use, use and method format. While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

Sequences

```
Diphtheria toxin
SEQ ID NO: 1:
GADDVVDSSKSFVMENFSSYHGTKPGYVDSIQKGIQKPKSGTQGNYDDDW

KGFYSTDNKYDAAGYSVDNENPLSGKAGGVVKVTYPGLTKVLALKVDNAE

TIKKELGLSLTEPLMEQVGTEEFIKRFGDGASRVVLSLPFAEGSSSVEYI

NNWEQAKALSVELEINFETRGKRGQDAMYEYMAQACAGNRVRRSVGSSLS

CINLDWDVIRDKTKTKIESLKEHGPIKNKMSESPNKTVSEEKAKQYLEEF

HQTALEHPELSELKTVTGTNPVFAGANYAAWAVNVAQVIDSETADNLEKT

TAALSILPGIGSVMGIADGAVHHNTEEIVAQSIALSSLMVAQAIPLVGEL

VDIGFAAYNFVESIINLFQVVHNSYNRPAYSPGHKTQPFLHDGYAVSWNT

VEDSIIRTGFQGESGHDIKITAENTPLPIAGVLLPTIPGKLDVNKSKTHI

SVNGRKIRMRCRAIDGDVTFCRPKSPVYVGNGVHANLHVAFHRSSSEKIH

SNEISSDSIGVLGYQKTVDHTKVNSKLSLFFEIKS

Receptor-binding domain of diphtheria toxin (amino
acids 385-535 of SEQ ID NO: 1)
SEQ ID NO: 2:
KTQPFLHDGYAVSWNTVEDSIIRTGFQGESGHDIKITAENTPLPIAGVLL

PTIPGKLDVNKSKTHISVNGRKIRMRCRAIDGDVTFCRPKSPVYVGNGVH

ANLHVAFHRSSSEKIHSNEISSDSIGVLGYQKTVDHTKVNSKLSLFFEIK

S

Receptor-binding domain of diphtheria toxin (amino
acids 387-535 of SEQ ID NO: 1)
SEQ ID NO: 3:
QPFLHDGYAVSWNTVEDSIIRTGFQGESGHDIKITAENTPLPIAGVLLPT

IPGKLDVNKSKTHISVNGRKIRMRCRAIDGDVTFCRPKSPVYVGNGVHAN

LHVAFHRSSSEKIHSNEISSDSIGVLGYQKTVDHTKVNSKLSLFFEIKS
```

EXPERIMENTAL EXAMPLES

Materials and Methods

Generation of DCOne Mature Dendritic Cells (mDC)

DCOne progenitors (as deposited with the DSMZ under accession number DSMZ ACC3189 on 15 Nov. 2012) were differentiated and matured according to the procedure described in WO2009019320 A2, the disclosure of which is incorporated by reference herein in its entirety. Cells were counted and phenotypic analysis of DCOne mDC cells was performed using flow cytometry (FACSVerse; BDBiosciences).

Culture of Ovarian Cancer Cells

OV90 ovarian cancer cell were cultured in medium199/MCDB105 medium (1:1) containing 15% FBS and 2% P/S) in an incubator at 37° C. with 5% $CO_2$ OV90 cells were obtained from ATCC.

Uptake of Foreign Antigens by DCOne mDC

Uptake by DCOne mDC was assessed for three different foreign antigens at a final concentration of 10 μg/mL for 4 hours and 24 hours during maturation. 750.000 cells were seeded into 6 well plates for each condition. The antigens used were CRM197-Alexa488, subunit KLH-FITC and β-galactosidase-FITC. CRM197-Alexa488 was purchased from Fina Biosolutions. Subunit KLH was purchased from Stellar Biotechnologies Inc. β-galactosidase was purchased from Roche. Subunit KLH and β-galactosidase were conjugated in-house to fluorochrome fluorescein isothiocyanate (FITC) using a FITC labelling kit according to manufacturer's protocol. Uptake of foreign antigens was assessed by flow cytometry. 0.08% Trypan blue was used to quench externally bound protein, to visualize only the internalized protein.

Labelling of Tumor Cells with Foreign Antigens

The labelling of OV90 ovarian cancer cells was assessed for three different foreign proteins at a final concentration of 10 μg/mL for 4 hours and 24 hours. 100.000 cells were seeded into 96 well plates for each condition. The proteins used were CRM197-Alexa488, Subunit KLH-FITC and β-galactosidase-FITC. Labelling of tumor cells in vitro was assessed by flow cytometry as mentioned above for DCOne mDC cells.

Humanized U87-MG Glioblastoma Mouse Model

Four-week-old immunodeficient female NOD/Shi-scid/IL-2Rγnull immunodeficient mouse strain (NCG; Taconic) were engrafted with intravenous (IV) injection of 5e4 cord blood-derived CD34+ hematopoietic stem and progenitor cells (French Blood Bank) two days after chemical myeloablative treatment. Humanized mice were enhanced for dendritic cell populations with a GM-CSF/IL3/IL4 hydrodynamic boost and Flt3L recombinant protein. After 7 days mice were inoculated subcutaneously in the right flank with $1e^6$ U87-MG glioblastoma cells/mouse (Sigma Aldrich) for tumor engraftment. Approximately 15 days after tumor engraftment mice were randomised and divided into different vaccination groups including 5 mice per group. All mice received 1 intraperitoneal (i.p.) vaccination and one intratumoral (i.t.) injection marking the tumor.

Mice received 100 μg KLH per i.p. injection or a 100 μl PBS i.p. injection, and were injected with 200.000 KLH-loaded DCOne mDCs i.t. or 100 μg KLH in 50 μl i.t. according to following schedule:
- Group 1 (PBS/KLH) received one i.p. PBS vaccination (on day 1 after randomization), and one i.t. injection with KLH (on day 8 after randomization);
- Group 2 (KLH/KLH) received one i.p. KLH vaccination (on day 1 after randomization), and one i.t. injection with KLH (on day 8 after randomization);
- Group 3 (PBS/KLH loaded DCOne) received one i.p. PBS vaccination (on day 1 after randomization), and one i.t. injection with KLH loaded DCOne mDC (on day 8 after randomization);
- Group 4 (KLH/KLH loaded DCOne) received one i.p. KLH vaccination (on day 1 after randomization), and one i.t. injection with KLH loaded DCOne mDC (on day 8 after randomization).

Subunit KLH was purchased from Stellar Biotechnologies Inc. Tumor growth reduction and induction of immune responses were measured.

Humanized A375 Melanoma Mouse Model

After humanization with $CD34^+$ stem cells and hydrodynamic boost with cytokines as described above, mice were inoculated subcutaneously in the right flank with $2e^6$ A375 melanoma cells/mouse (Sigma Aldrich) for tumor engraftment. Approximately 15 days after tumor engraftment mice were randomized and divided into different vaccination groups including 5 mice per group. The mice received two intraperitoneal (i.p.) vaccinations and thereafter one intratumoral (i.t.) injection for marking the tumor.

Mice received 100 μg KLH in 100 μl per i.p. injection or a 100 μl PBS i.p. injection, and were injected with 200.000 KLH-loaded DCOne mDCs or 100 μg KLH in 50 μl i.t. according to the following schedule:
- Group 1 (PBS/KLH) received two i.p. PBS vaccinations (on days 1 and 8 after randomization), and one i.t. injection with KLH (on day 15 after randomization);
- Group 2 (KLH/KLH) received two i.p. KLH vaccinations (on days 1 and 8 after randomization), and one i.t. injection with KLH (on day 15 after randomization);
- Group 3 (PBS/KLH loaded DCOne) received two i.p. PBS vaccinations (on days 1 and 8 after randomization), and one i.t. injection with KLH loaded DCOne mDC (on day 15 after randomization);
- Group 4 (KLH/KLH loaded DCOne) received two i.p. KLH vaccinations (on days 1 and 8 after randomization), and one i.t. injection with KLH loaded DCOne mDC (on day 15 after randomization).

Subunit KLH was purchased from Stellar Biotechnologies Inc. Tumor growth reduction and vaccination induced immune responses were measured.

Example 1. Uptake of Foreign Proteins

Uptake of Subunit KLH-FITC by DCOne mDC

Figure 1A:
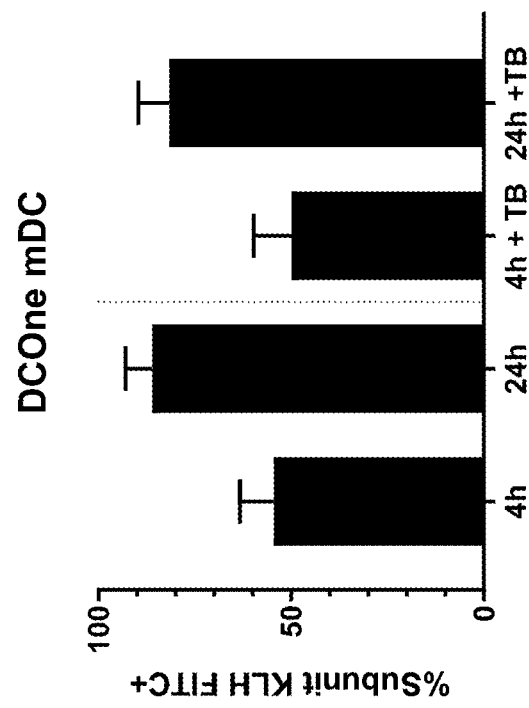

DCOne mDC cells were loaded with fluorochrome-conjugated subunit KLH during maturation process for 4 hours and 24 hours as described in the material and methods section. The internalization of subunit KLH was analysed using flow cytometer. Trypan blue quenches the cell surface-bound antigen and was used to distinguish between surface-bound antigen and internalized antigen. The observed internalization of subunit KLH-FITC by DCOne mDC after 4 hrs was 54.6±8.8%, and 49.9±9.8% with trypan blue and after 24 hours 86.1±7.0%, and 81.7±8.0% with trypan blue indicating effective antigen uptake by DCOne mDC (FIG. 1A).

Labelling of OV90 Tumor Cells with Subunit KLH

OV90 ovarian carcinoma cells were cultured with subunit KLH-FITC for 4 hours and 24 hours as described in the material and methods section. It was observed that 13.5±2.6%, labelling of OV90 for 4 hours of which 7.5±1.0% of cells with intracellular antigen as demonstrated by quenching of surface-bound subunit KLH-FITC signal with trypan blue, and after 24 hours 16.5±11.5% of OV90 cells were labelled with antigen with 9.5±3.8% of antigen inside the cells (FIG. 1B).

Uptake of β-Galactosidase-FITC by DCOne mDC

DCOne mDCs were incubated with β-galactosidase-FITC for 4 hrs and 24 hrs as described in the materials and methods section. The uptake of β-galactosidase-FITC was measured using flow cytometry in the absence or presence of trypan blue in order to distinguish between extracellularly bound and internalized β-galactosidase-FITC. FIG. 2A depicts that after 4 hrs incubation 39.7±10.7% of DCOne mDC have internalized β-galactosidase-FITC as the trypan blue quenching hardly affected the signal (34.5±10.2%) indicating intracellular localization of β-galactosidase-FITC in DCOne mDC. The internalisation of β-galactosidase-FITC by DCOne mDC was increased after 24 hours i.e., 57.6±10.2%, and 49.9±13.0% with trypan blue indicating intracellular β-galactosidase-FITC.

Labelling of OV90 by β-Galactosidase-FITC

Figure 2B:
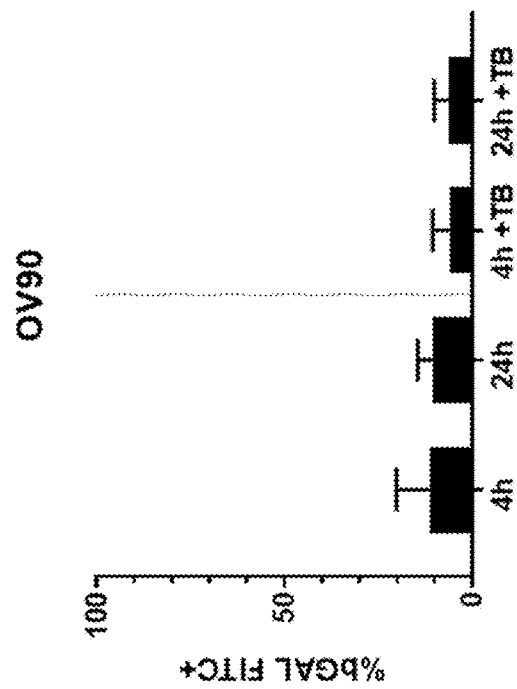
FIG. 2A-FIG. 2B depict the uptake of β-galactosidase protein by DCOne mDC cells (n=3) (FIG. 2A) and the labelling of OV90 ovarian cancer cells (n=2) (FIG. 2B) after 4 hours and 24 hours. 0.08% trypan blue was added to quench extracellular bound β-galactosidase-FITC to visualize the percentage intracellular β-galactosidase-FITC.
Figure 2A:
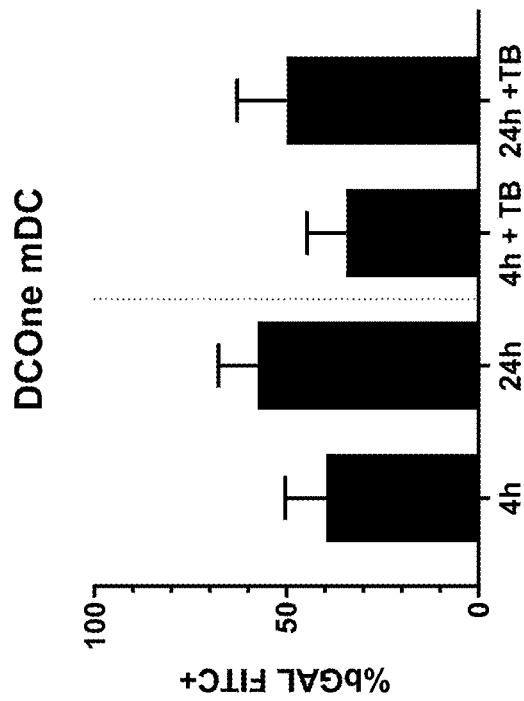

The labelling of ovarian cancer cell line OV-90 with β-galactosidase-FITC after 4 hours and 24 hours was 11.3±8.9% (6.0±4.6% with trypan blue) and 10.4±4.2%, (6.5±3.6% with trypan blue) respectively showing both surface-bound and intracellular presence of β-galactosidase-FITC (FIG. 2B).

Uptake of CRM197 by DCOne mDC

Figure 7B:
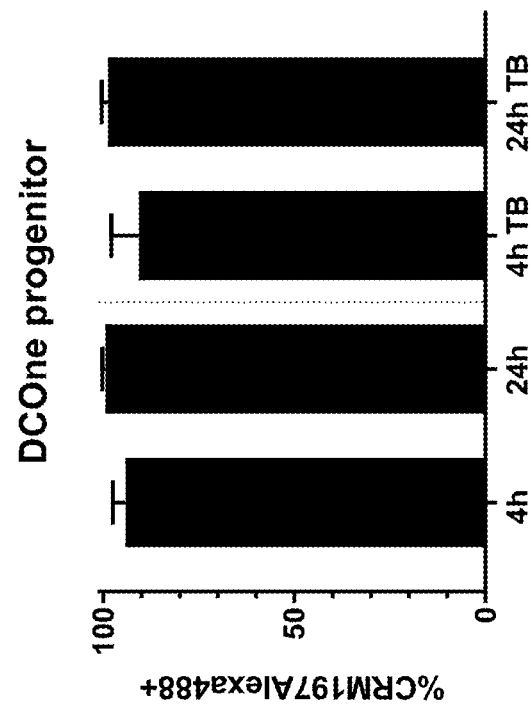
FIG. 7A-FIG. 7D depict the uptake of CRM197 protein by DCOne mDC cells (n=2) (FIG. 7A) and labelling of DCOne progenitor AML cells (n=4) (FIG. 7B), OV90 ovarian cancer cells (n=2) (FIG. 7C), and U87 MG glioblastoma cancer cells (n=3) (FIG. 7D) after 4 hours and 24 hours. 0.08% trypan blue was added to quench extracellular bound CRM197-Alexa488 to visualize the percentage intracellular CRM197-Alexa488.
Figure 7A:
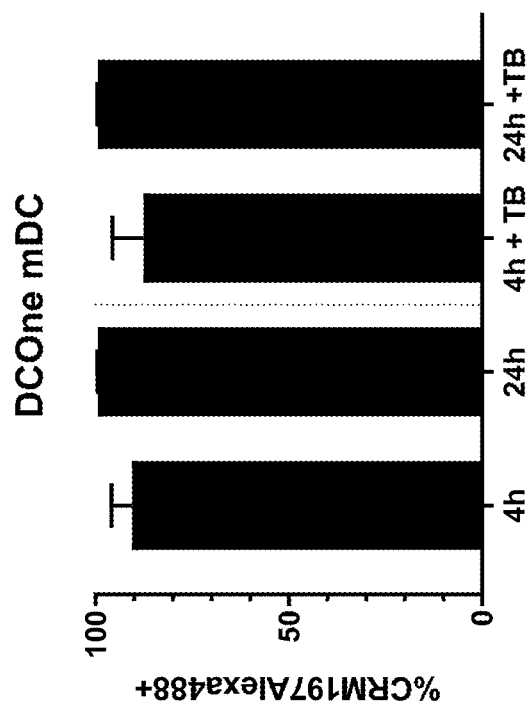

During the maturation process, DCOne mDC cells were cultured with CRM197-Alexa488 for 4 and 24 hours as described in the materials and methods section. After 4 and 24 hours uptake of antigen CRM-197 by DCOne mDCs were analysed using a flow cytometer in the presence and absence of trypan blue as mentioned in above sections. 90.6±5.4% and 99.4±0.1% of DCOne mDC were observed to have had efficiently internalized CRM-197 after 4 and 24 hours, respectively. Trypan blue quenching did not affect these results (87.6±8.0 and 99.5±0.2% respectively; FIG. 7A).

Labelling of OV90 Tumor Cells with CRM197

Figure 3:
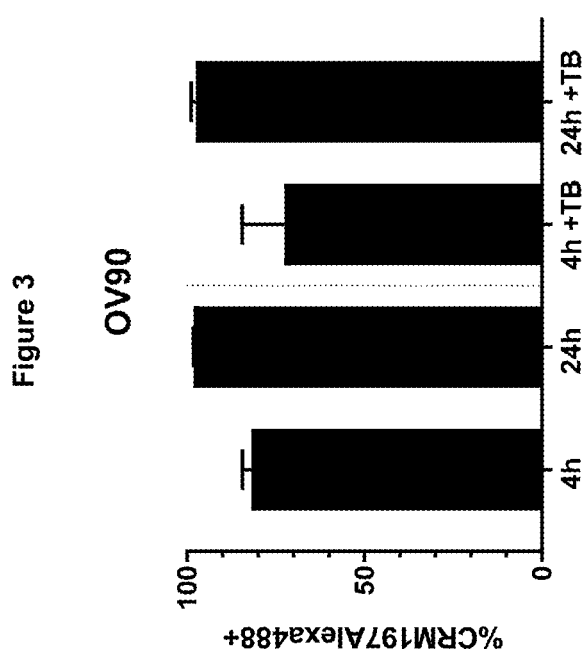
FIG. 3 depicts the uptake of CRM197 protein by OV90 ovarian cancer cells (n=2) after 4 hours and 24 hours. 0.08% trypan blue was added to quench extracellular bound CRM197-Alexa488 to visualize the percentage intracellular CRM197-Alexa488.

The percentage of CRM197-Alexa488 uptake after 4 hours by OV90 tumor cells was 82.0±2.5%, and after 24 hours labelling increased up to 98.2±0.1% (FIG. 3). The trypan blue quenching did not affect the signal indicating that CRM-197 is predominantly present inside the cell (72.7±11.9% and 97.6±1.4% with trypan blue after 4 and 24 hours respectively).

The in vitro data of uptake of foreign proteins by DCOne mDCs showed that DCOne mDCs were very efficient in internalizing foreign protein. All foreign proteins tested, CRM197, KLH and β-galactosidase were taken up very well by DCOne mDCs. DCOne cells can thus be used as a carrier for vaccination and/or intratumoral delivery of foreign proteins.

The data of uptake of foreign proteins by ovarian cancer cells showed that ovarian cancer cells were more specific in internalizing foreign protein as compared to DCOne cells. CRM197 is taken up very efficiently by receptor-mediated endocytosis (Moya et al. *J Cell Biol*, 101(2):548-59 (1985), the disclosure of which is incorporated by reference herein in its entirety) in tumor cells due to presence of the specific HB-EGF receptor for diphtheria toxin/CRM197 as described in literature (e.g., Miyamoto et al. *Cancer Sci*, 97(5):341-7 (2006) the disclosure of which is incorporated by reference herein in its entirety), while uptake of KLH and β-galactosidase is lower. These findings show that a tumor can be marked by foreign proteins. This is especially the case for CRM197, which can therefore potentially be used as a carrier for tumor marking with other foreign protein coupled to CRM197.

Example 2. Tumor Growth Inhibition in a Humanized U87-MG Glioblastoma Mouse Model and in a Humanized A375 Melanoma Mouse Model The U87-MG mice received one i.p. vaccination of either PBS or KLH and one i.t. injection to mark the tumor either with KLH or KLH-loaded DCOne mDCs. Tumor growth was monitored three times per week using a digital caliper (FIG. 4A). Tumor volumes (in mm3) were calculated according to the following formula: Volume=(width× length^2)/2. At day 18, a slowed tumor growth was observed in vaccinated mice as compared to the mice injected with PBS, with i.t. injection of KLH-loaded DCOne having the strongest effect (FIG. 4B).

Figure 5B:
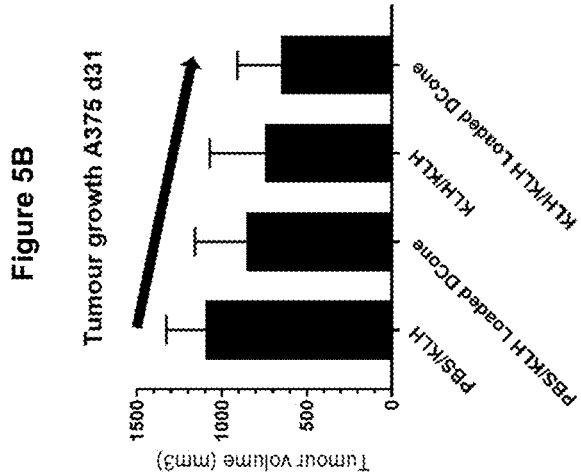
FIG. 5A-FIG. 5B depict tumor growth inhibition in a humanized A375 melanoma model. Tumor size was monitored three times per week using a digital caliper (FIG. 5A). Tumor size after day 30 in vaccinated mice injected as indicated is shown in FIG. 5B.
Figure 5A:
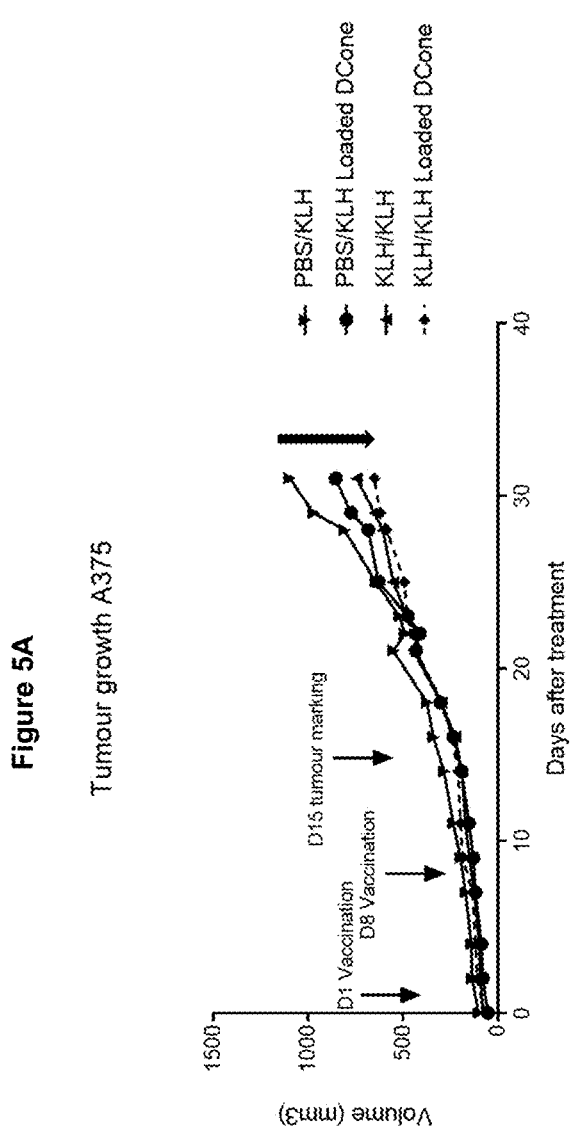

The A375 melanoma mice received two i.p. vaccinations of either PBS or KLH and one i.t. injection to mark the tumor either with KLH or KLH-loaded DCOne mDCs. Tumor growth was monitored three times per week using a digital caliper (FIG. 5A). Tumor volumes (in mm3) were calculated according to the following formula: Volume= (width× length^2)/2. As with the U87-MG mice, it was observed that the vaccinated group of mice had a slowed tumor growth compared to the groups injected with PBS (FIG. 5B). This effect was strongest in the mice treated with KLH/KLH loaded DCOne.

These in vivo data in humanized mice show that vaccination followed by intratumoral injection (tumor marking) leads to slowed tumor growth in two separate solid tumor models, particularly when tumor marking was carried out using DCOne mDCs as a carrier. Although not statistically significant, the trend of slowed tumor growth was consistent in two separate solid tumor models.

Example 3. T Cell Mediated KLH-Specific Antibody Production

Possible antibody responses against KLH resulting from intratumoral injection and/or vaccination were quantified by ELISA (D0, D14 and sacrifice). In both U87-MG and A375 mice, no significant difference was observed regarding anti-KLH IgM concentration between treated groups and the PBS control group over time (FIG. 6A-FIG. 6B). However, it was surprisingly observed that mice from the KLH/KLH loaded DCOne group produced significantly more anti-KLH IgG than the PBS control group at sacrifice (FIG. 6C-FIG. 6D). This indicates a T cell-dependent IgM to IgG switch (Geha et al., *NEJM*, 330:1008-1009 (1994) the disclosure of which is incorporated by reference herein in its entirety).

Example 4. CRM197 Vaccination

Materials and Methods
Generation of DCOne Mature Dendritic Cells (mDC)
DCOne progenitor cells (as deposited with the DSMZ under accession number DSMZ ACC3189 on 15 Nov. 2012) were differentiated and matured according to the procedure described in PCT Publication No. WO 2009/019320, incorporated herein by reference in its entirety. Cells were counted and phenotypic analysis of DCOne mDC cells was performed using flow cytometry (FACSVerse; BDBiosciences).
Culture of Cancer Cells
DCOne AML progenitor cells were cultured in MEMα containing 10% FBS and 2% P/S in an incubator at 37° C. with 5% $CO_2$. OV90 ovarian cancer cells were cultured in medium199/MCDB105 medium (1:1) containing 15% FBS and 2% P/S in an incubator at 37° C. with 5% CO2. OV90 cells were obtained from ATCC. U87MG glioblastoma cancer cells were cultured in EMEM medium containing 10% FBS and 2% P/S in an incubator at 37° C. with 5% CO2. U87MG cells were obtained from Merck.
Uptake of Foreign Antigen CRM197 by DCOne mDC
Uptake by DCOne mDC cells was assessed for foreign antigen at a final concentration of 10 µg/mL for 4 hours and 24 hours during maturation. 750,000 cells were seeded into 6-well plates for each condition. The foreign antigen used was CRM197-Alexa488 (Fina Biosolutions). Uptake of foreign antigens was assessed by flow cytometry. 0.08% Trypan blue was used to quench externally bound protein, to visualize only the internalized protein.
Labelling of Tumor Cells with Foreign Antigen CRM197
The labelling of DCOne progenitor AML cells, OV90 ovarian cancer cells and U87MG glioblastoma cancer cells was assessed at a final concentration of 10 µg/mL for 4 hours and 24 hours. 100,000 cells were seeded into 96 well plates for each condition. The foreign antigen used was CRM197-Alexa488 (Fina Biosolutions). Labelling of tumor cells in vitro was assessed by flow cytometry as mentioned above for DCOne mDCs.
Humanized OV90luc Ovarian Cancer Mouse Model
NSGS were engrafted with intravenous (IV) injection of 5e4 cord blood-derived CD34+ hematopoietic stem and progenitor cells. Mice were inoculated subcutaneously with 5e6 OV90luc ovarian cancer cells expressing luciferase for tumor engraftment. Mice were randomized by tumor volume and divided into different vaccination groups including 5 mice per group. The average tumour size at start of vaccination was 80 $mm^3$. All mice received 2 intraperitoneal (i.p.) vaccinations and one intratumoral (i.t.) injection marking the tumor.
Mice received 50 µg CRM197 per i.p. injection or a PBS i.p. injection, and were injected with 25 µg CRM197 i.t. according to the following schedule:
Group 1 (PBS/PBS) received two i.p. PBS vaccinations (week 2 and 3 after randomization), and one i.t. injection with PBS (week 4 after randomization).

Group 2 (PBS/CRM197) received two i.p. PBS vaccinations (week 2 and 3 after randomization), and one i.t. injection with CRM197 (week 4 after randomization).

Group 3 (CRM197/PBS) received two i.p. CRM197 vaccinations (week 2 and 3 after randomization), and one i.t. injection with PBS (week 4 after randomization).

Group 4 (CRM197/CRM197) received two i.p. CRM197 vaccinations (week 2 and 3 after randomization), and one i.t. injection with CRM197 (week 4 after randomization).

CRM197 was purchased from Fina Biosolutions. Tumor growth reduction (caliper measurement and BLI imaging) and induction of immune responses were measured.

Uptake of CRM197 by DCOne mDC

During the maturation process, DCOne mDC cells were cultured with CRM197-Alexa488 for 4 and 24 hours as described in the materials and methods section. After 4 and 24 hours uptake of antigen CRM-197 by DCOne mDC cells were analysed using a flow cytometer in the presence and absence of trypan blue as mentioned in above sections. 90.6±5.4% and 99.4±0.1% of DCOne mDC cells were observed to have had efficiently internalized CRM-197 after 4 and 24 hours, respectively. Trypan blue quenching did not affect these results (87.6±8.0% and 99.5±0.2% respectively; FIG. 7A).

Labelling of DCOne Progenitor Cells with CRM197

The percentage of CRM197-Alexa488 uptake after 4 hours by DCOne progenitor cells was 94.2±3.3%, and after 24 hours labelling increased up to 99.5±0.8%. The trypan blue quenching did not affect the signal indicating that CRM197 is predominantly present inside the cell (90.7±7.3% and 98.8±1.7% with trypan blue after 4 and 24 hours respectively; FIG. 7B).

Labelling of OV90 Tumor Cells with CRM197

Figure 7D:
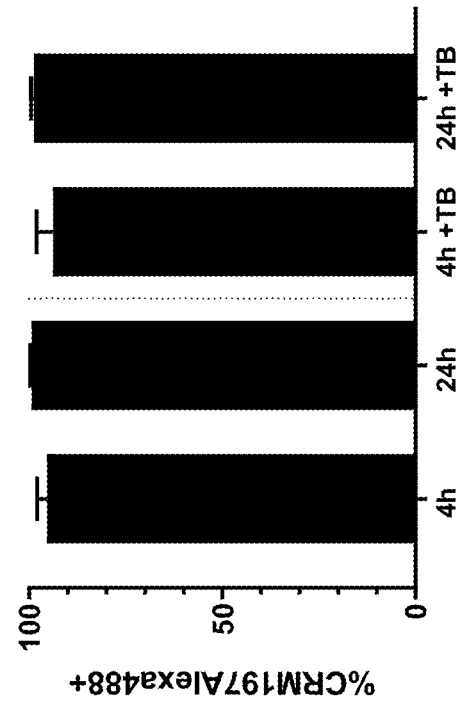
Figure 7C:
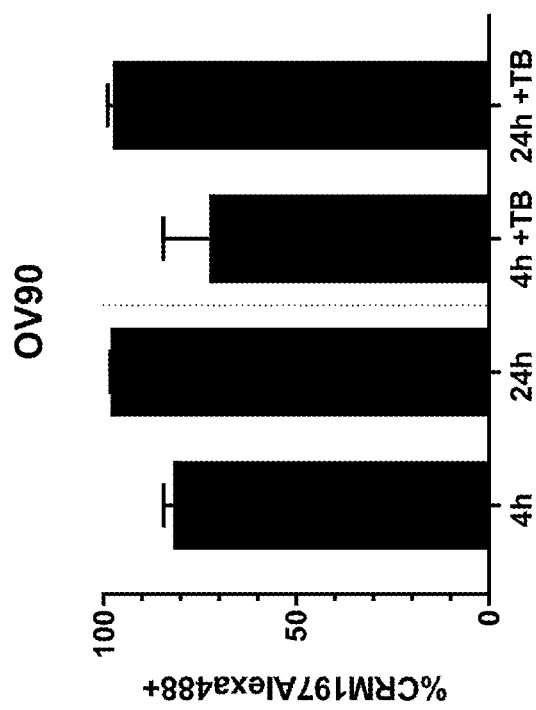

The percentage of CRM197-Alexa488 uptake after 4 hours by OV90 tumor cells was 82.0±2.5%, and after 24 hours labelling increased up to 98.2±0.1%. The trypan blue quenching did not affect the signal indicating that CRM197 is predominantly present inside the cell (72.7±11.9% and 97.6±1.4% with trypan blue after 4 and 24 hours respectively; FIG. 7C).

Labelling of U87MG Tumor Cells with CRM197

The percentage of CRM197-Alexa488 uptake after 4 hours by U87MG tumor cells was 95.3±2.6%, and after 24 hours labelling increased up to 99.4±0.4%. The trypan blue quenching did not affect the signal indicating that CRM197 is predominantly present inside the cell (93.9±4.2% and 98.8±0.7% with trypan blue after 4 and 24 hours respectively; FIG. 7D).

Tumor Growth in a Humanized OV90luc Ovarian Cancer Model

Tumor growth was monitored by weekly calliper measurements and optical imaging from the beginning of treatment. The OV90luc mice received two i.p. vaccinations of either PBS or CRM197 and one i.t. injection to mark the tumor either with PBS or CRM197. Tumor growth was monitored per week using a digital caliper. Tumor volumes (in mm$^3$) were calculated by the ellipsoid formula (L×W×H)π/6.

No difference in tumor volume was found in CRM197 vaccinated mice as compared to the mice injected with PBS (FIG. 8A). Bioluminescence data showed that CRM197 vaccinated mice followed by i.t. injection of CRM197 exhibited a significantly lower bioluminescence intensity (FIG. 8B and FIG. 9). This is indicative of a significant growth arrest of OV90 ovarian cancer cells in this CRM197 vaccinated/CRM197 i.t. group.

These in vivo data in humanized mice show that CRM197 vaccination followed by intratumoral injection (tumor marking) of CRM197 leads to cancer cell growth arrest.

Example 5. Proof-of-Concept In Vivo Cytotoxicity CRM197

CRM197 is used to study a tumor antigen-independent prime-boost strategy using CRM197 as a tumor-independent antigen in a humanized tumor mouse model. Goals of this study are: optimization of a vaccination protocol; repetition of an earlier experiment using an optimal mouse model for robust tumor regression; and assessment of tumors using immunohistochemistry for immune activation at the tumor site.

Vaccination Strategy

Intraperitoneal vaccination:
(week −1, pre-engraftment; week 1, post-engraftment)
I. Vaccination with saline (6 mice).
II. Vaccination with saline (6 mice).
III. Vaccination with CRM197 (6 mice).
IV. Vaccination with CRM197 (6 mice).

Intratumoral injection:
(week 3 post-engraftment)
I. Intra-tumoral vaccination with saline (6 mice).
II. Intra-tumoral vaccination with CRM197 (6 mice).
III. Intra-tumoral vaccination with saline (6 mice).
IV. Intra-tumoral vaccination with CRM197 (6 mice).

The studies are performed in mice with an HB-EGF-expressing tumor using the U87MG glioblastoma cell line. The clinical readout is tumor regression/clearance and survival. Immunohistochemistry of the tumors is assessed to determine tumor infiltration of immune cells. A serum analysis is performed to detect anti-CRM antibodies. The vaccination dose is 50 μg CRM197/mouse. The intratumoral dose is 25 μg CRM197/mouse.

TABLE 1

Tabular overview of the CRM197 experiment

| Group | # of mice | Tumor engraftment Week 0 | Vaccination (i.p.) Week −1&1 | Intratumoral injection Week 3 |
|---|---|---|---|---|
| #1 | 6 | U87MG | Saline | Saline |
| #2 | 6 | U87MG | Saline | CRM197 |
| #3 | 6 | U87MG | CRM197 | Saline |
| #4 | 6 | U87MG | CRM197 | CRM197 |

What is claimed is:

1. A method for generating an immune response against a solid tumor in a subject comprising:
   a vaccination step comprising administering a first composition to the subject at a site distal to a solid tumor site, wherein the first composition comprises a CD34-positive, CD1a-positive, and CD83-positive cell comprising CRM197 or a nucleic acid encoding CRM197; and
   a tumor-marking step comprising administering a second composition to the subject at the solid tumor site, wherein the second composition comprises CRM197 or a nucleic acid encoding CRM197, thereby generating an immune response against the solid tumor in the subject.

2. The method of claim 1, wherein the CD34-positive, CD1a-positive, and CD83-positive cell is differentiated from DCOne.

3. The method of claim 1, wherein the tumor-marking step comprises administering the second composition into the tumor.

4. The method of claim 1, wherein the vaccination step comprises administering the first composition into an organ system that is different to the organ system in which the tumor resides.

5. The method of claim 1, wherein the vaccination step comprises administering the first composition into a site contralateral to the tumor.

6. The method of claim 1, wherein the vaccination step comprises administering the first composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue.

7. The method of claim 1, wherein the second composition further comprises a tumor targeting component selected from the group consisting of a tumor-specific virus, an oncolytic virus, and a tumor-specific nanoparticle.

8. The method of claim 1, wherein the solid tumor is glioblastoma or ovarian cancer.

9. The method of claim 1, wherein the subject is selected from the group consisting of a human, a domesticated animal, and an animal suitable for veterinary healthcare.

10. A method for generating an immune response against a solid tumor in a subject comprising:
    a vaccination step comprising administering a first composition to the subject at a site distal to a solid tumor site, wherein the first composition comprises CRM197 or a nucleic acid encoding CRM197; and
    a tumor-marking step comprising administering a second composition to the subject at the solid tumor site, wherein the second composition comprises a CD34-positive, CD1a-positive, and CD83-positive cell comprising CRM197 or a nucleic acid encoding CRM197, thereby generating an immune response against the solid tumor in the subject.

11. The method of claim 10, wherein the CD34-positive, CD1a-positive, and CD83-positive cell is differentiated from DCOne.

12. The method of claim 10, wherein the tumor-marking step comprises administering the second composition into the tumor.

13. The method of claim 10, wherein the vaccination step comprises administering the first composition into an organ system that is different to the organ system in which the tumor resides.

14. The method of claim 10, wherein the vaccination step comprises administering the first composition into a site contralateral to the tumor.

15. The method of claim 10, wherein the vaccination step comprises administering the first composition via a route selected from the group consisting of intramuscular, subcutaneous, intravenous, intraarterial, intraperitoneal, intrasternal, intradermal, transcutaneous, transdermal, delivery to the interstitial space of a tissue, and delivery to a non-tumor tissue.

16. The method of claim 10, wherein the second composition further comprises a tumor targeting component selected from the group consisting of a tumor-specific virus, an oncolytic virus, and a tumor-specific nanoparticle.

17. The method of claim 10, wherein the solid tumor is glioblastoma or ovarian cancer.

18. The method of claim 10, wherein the subject is selected from the group consisting of a human, a domesticated animal, and an animal suitable for veterinary healthcare.

19. A method for generating an immune response against a solid tumor in a subject comprising:
- a vaccination step comprising administering a first composition to the subject at a site distal to a solid tumor site, wherein the first composition comprises a first CD34-positive, CD1a-positive, and CD83-positive cell comprising CRM197 or a nucleic acid encoding CRM197; and
- a tumor-marking step comprising administering a second composition to the subject at the solid tumor site, wherein the second composition comprises a second CD34-positive, CD1a-positive, and CD83-positive cell comprising CRM197 or a nucleic acid encoding CRM197,
- thereby generating an immune response against the solid tumor in the subject.

20. The method of claim 19, wherein the first and the second CD34-positive, CD1a-positive, and CD83-positive cell are differentiated from DCOne.

* * * * *

SEQUENCE LISTING

<160> NUMBER OF SEQ ID NOS: 3

<210> SEQ ID NO 1
<211> LENGTH: 535
<212> TYPE: PRT
<213> ORGANISM: Corynebacterium diphtheriae

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

```
Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 2
<211> LENGTH: 151
<212> TYPE: PRT
<213> ORGANISM: Artificial Sequence
<220> FEATURE:
<223> OTHER INFORMATION: Amino acids 385-535 of SEQ ID NO:1

<400> SEQUENCE: 2

Lys Thr Gln Pro Phe Leu His Asp Gly Tyr Ala Val Ser Trp Asn Thr
1               5                   10                  15

Val Glu Asp Ser Ile Ile Arg Thr Gly Phe Gln Gly Glu Ser Gly His
            20                  25                  30

Asp Ile Lys Ile Thr Ala Glu Asn Thr Pro Leu Pro Ile Ala Gly Val
        35                  40                  45

Leu Leu Pro Thr Ile Pro Gly Lys Leu Asp Val Asn Lys Ser Lys Thr
    50                  55                  60

His Ile Ser Val Asn Gly Arg Lys Ile Arg Met Arg Cys Arg Ala Ile
65                  70                  75                  80

Asp Gly Asp Val Thr Phe Cys Arg Pro Lys Ser Pro Val Tyr Val Gly
                85                  90                  95

Asn Gly Val His Ala Asn Leu His Val Ala Phe His Arg Ser Ser Ser
            100                 105                 110

Glu Lys Ile His Ser Asn Glu Ile Ser Ser Asp Ser Ile Gly Val Leu
        115                 120                 125

Gly Tyr Gln Lys Thr Val Asp His Thr Lys Val Asn Ser Lys Leu Ser
    130                 135                 140

Leu Phe Phe Glu Ile Lys Ser
145                 150

<210> SEQ ID NO 3
<211> LENGTH: 149
<212> TYPE: PRT
<213> ORGANISM: Artificial Sequence
<220> FEATURE:
<223> OTHER INFORMATION: Amino acids 387-535 of SEQ ID NO:1

<400> SEQUENCE: 3

Gln Pro Phe Leu His Asp Gly Tyr Ala Val Ser Trp Asn Thr Val Glu
1               5                   10                  15

Asp Ser Ile Ile Arg Thr Gly Phe Gln Gly Glu Ser Gly His Asp Ile
            20                  25                  30
```

-continued

```
Lys Ile Thr Ala Glu Asn Thr Pro Leu Pro Ile Ala Gly Val Leu Leu
        35                  40                  45

Pro Thr Ile Pro Gly Lys Leu Asp Val Asn Lys Ser Lys Thr His Ile
    50                  55                  60

Ser Val Asn Gly Arg Lys Ile Arg Met Arg Cys Arg Ala Ile Asp Gly
65                  70                  75                  80

Asp Val Thr Phe Cys Arg Pro Lys Ser Pro Val Tyr Val Gly Asn Gly
                85                  90                  95

Val His Ala Asn Leu His Val Ala Phe His Arg Ser Ser Ser Glu Lys
            100                 105                 110

Ile His Ser Asn Glu Ile Ser Ser Asp Ser Ile Gly Val Leu Gly Tyr
        115                 120                 125

Gln Lys Thr Val Asp His Thr Lys Val Asn Ser Lys Leu Ser Leu Phe
    130                 135                 140

Phe Glu Ile Lys Ser
145
```